US011718835B2

(12) United States Patent
Lock et al.

(10) Patent No.: US 11,718,835 B2
(45) Date of Patent: *Aug. 8, 2023

(54) SCALABLE PURIFICATION METHOD FOR AAV8

(71) Applicant: The Trustees of the University of Pennsylvania, Philadelphia, PA (US)

(72) Inventors: Martin Lock, Southampton, PA (US); Mauricio Alvira, Philadelphia, PA (US)

(73) Assignee: Ths Trustees of the University of Pennsylvania, Philadelphia, PA (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/328,686

(22) Filed: May 24, 2021

(65) Prior Publication Data
US 2021/0277364 A1 Sep. 9, 2021

Related U.S. Application Data

(63) Continuation of application No. 16/060,408, filed as application No. PCT/US2016/065976 on Dec. 9, 2016, now Pat. No. 11,015,174.

(60) Provisional application No. 62/322,098, filed on Apr. 13, 2016, provisional application No. 62/266,341, filed on Dec. 11, 2015.

(51) Int. Cl.
| | |
|---|---|
| C12N 7/02 | (2006.01) |
| C12N 7/00 | (2006.01) |
| B01D 15/38 | (2006.01) |
| B01J 20/281 | (2006.01) |
| C12N 15/864 | (2006.01) |
| G01N 21/33 | (2006.01) |
| B01J 41/05 | (2017.01) |
| B01D 15/16 | (2006.01) |
| B01D 15/36 | (2006.01) |
| B01J 41/20 | (2006.01) |

(52) U.S. Cl.
CPC ........... *C12N 7/02* (2013.01); *B01D 15/3804* (2013.01); *B01J 20/281* (2013.01); *C12N 7/00* (2013.01); *C12N 15/8645* (2013.01); *G01N 21/33* (2013.01); *B01D 15/166* (2013.01); *B01D 15/363* (2013.01); *B01J 41/05* (2017.01); *B01J 41/20* (2013.01); *C12N 2750/14143* (2013.01); *C12N 2750/14151* (2013.01)

(58) Field of Classification Search
CPC ........ C12N 7/02; C12N 7/00; C12N 15/8645; C12N 2750/14143; C12N 2750/14151; B01D 15/3804; B01D 15/166; B01D 15/363; B01J 20/281; B01J 41/05; B01J 41/20; G01N 21/33

See application file for complete search history.

(56) References Cited

U.S. PATENT DOCUMENTS

| | | |
|---|---|---|
| 5,658,785 A | 8/1997 | Johnson |
| 6,566,118 B1 | 5/2003 | Atkinson et al. |
| 6,593,123 B1 | 7/2003 | Wright et al. |
| 6,723,551 B2 | 4/2004 | Kotin et al. |
| 6,759,237 B1 | 7/2004 | Wilson et al. |
| 6,893,865 B1 | 5/2005 | Lockert et al. |
| 7,105,345 B2 | 9/2006 | Wilson et al. |
| 7,186,552 B2 | 3/2007 | Wilson et al. |
| 7,282,199 B2 | 10/2007 | Gao et al. |
| 7,588,772 B2 | 9/2009 | Kay et al. |
| 7,790,449 B2 | 9/2010 | Gao et al. |
| 7,906,111 B2 | 3/2011 | Wilson et al. |
| 8,137,948 B2 | 3/2012 | Qu et al. |
| 8,319,480 B2 | 11/2012 | Ko et al. |
| 8,927,514 B2 | 1/2015 | Chatterjee et al. |
| 8,962,330 B2 | 2/2015 | Gao et al. |
| 8,962,332 B2 | 2/2015 | Gao et al. |
| 9,102,949 B2 | 8/2015 | Gao et al. |
| 9,198,984 B2 | 12/2015 | Lock et al. |
| 10,155,931 B2 | 12/2018 | Lock et al. |
| 11,015,173 B2 | 5/2021 | Lock et al. |
| 11,015,174 B2 | 5/2021 | Lock et al. |
| 11,028,372 B2 | 6/2021 | Lock et al. |
| 11,098,286 B2 | 8/2021 | Lock et al. |
| 2002/0127582 A1 | 9/2002 | Atkinson et al. |
| 2004/0110266 A1 | 6/2004 | Chiorini et al. |
| 2005/0014262 A1 | 1/2005 | Gao et al. |
| 2005/0024467 A1 | 2/2005 | Verbrook |
| 2006/0204479 A1 | 9/2006 | Wilson et al. |

(Continued)

FOREIGN PATENT DOCUMENTS

| | | |
|---|---|---|
| EP | 0282177 | 9/1988 |
| EP | 1486567 A1 | 12/2004 |

(Continued)

OTHER PUBLICATIONS

Adachi et al., Drawing a high-resolution functional map of adeno-associated virus capsid by massively parallel sequencing, Nat Commun, vol. 5:3075, Jan. 2014.

(Continued)

*Primary Examiner* — Rachel B Gill

(74) *Attorney, Agent, or Firm* — Howson & Howson LLP; Cathy A Kodroff

(57) ABSTRACT

A two-step chromatography purification scheme is described which selectively captures and isolates the genome-containing rAAV vector particles from the clarified, concentrated supernatant of a rAAV production cell culture. The process utilizes an affinity capture method performed at a high salt concentration followed by an anion exchange resin method performed at high pH to provide rAAV vector particles which are substantially free of rAAV intermediates.

24 Claims, 5 Drawing Sheets

Specification includes a Sequence Listing.

(56) References Cited

U.S. PATENT DOCUMENTS

| | | |
|---|---|---|
| 2007/0036760 A1 | 2/2007 | Wilson et al. |
| 2008/0008684 A1 | 1/2008 | Wilson et al. |
| 2008/0050343 A1 | 2/2008 | Wilson et al. |
| 2008/0050345 A1 | 2/2008 | Wilson et al. |
| 2008/0050770 A1 | 2/2008 | Zhang et al. |
| 2008/0075737 A1 | 3/2008 | Gao et al. |
| 2008/0075740 A1 | 3/2008 | Gao et al. |
| 2009/0275107 A1 | 11/2009 | Lock et al. |
| 2013/0045186 A1 | 2/2013 | Gao et al. |
| 2013/0059732 A1 | 3/2013 | Lisowski et al. |
| 2014/0044794 A1 | 2/2014 | Okada et al. |
| 2015/0024467 A1 | 1/2015 | Sheldon et al. |
| 2015/0349911 A1 | 12/2015 | Otsubo |
| 2019/0002841 A1 | 1/2019 | Lock et al. |
| 2019/0002842 A1 | 1/2019 | Lock et al. |
| 2019/0002843 A1 | 1/2019 | Lock et al. |
| 2019/0055523 A1 | 2/2019 | Lock et al. |
| 2021/0238560 A1 | 8/2021 | Lock et al. |
| 2021/0348132 A1 | 11/2021 | Lock et al. |
| 2021/0348133 A1 | 11/2021 | Lock et al. |

FOREIGN PATENT DOCUMENTS

| | | |
|---|---|---|
| EP | 1127150 B1 | 5/2007 |
| EP | 2018421 B1 | 12/2012 |
| EP | 3054007 | 2/2015 |
| JP | 2007/117003 A | 5/2007 |
| JP | 5268890 | 5/2013 |
| WO | WO-1999/011764 | 3/1999 |
| WO | WO-1999/015685 | 4/1999 |
| WO | WO-2000/028061 A2 | 5/2000 |
| WO | WO-2003/052051 A2 | 6/2003 |
| WO | WO-2004/113494 | 12/2004 |
| WO | WO-2005/005610 A2 | 1/2005 |
| WO | WO-2005/033321 | 4/2005 |
| WO | WO-2006/110689 A2 | 10/2006 |
| WO | WO-2007/127264 | 11/2007 |
| WO | WO-2008/027084 A2 | 3/2008 |
| WO | WO 2009/088786 | 7/2009 |
| WO | WO 2009/108274 | 9/2009 |
| WO | WO 2011/094198 | 8/2011 |
| WO | WO 2012/112832 | 8/2012 |
| WO | WO-2014/124282 | 8/2014 |
| WO | WO 2014/125101 | 8/2014 |
| WO | WO-2016/049230 | 3/2016 |
| WO | WO 2016/128408 A1 | 8/2016 |
| WO | WO-2016/200543 | 12/2016 |
| WO | WO 2019/212921 | 11/2019 |
| WO | WO2019241535 A2 | 12/2019 |

OTHER PUBLICATIONS

Brument et al., A Versatile and Scalable Two-Step Ion-Exchange Chromatography Process for the Purification of Recombinant Adeno-associated Virus Serotypes-2 and -5, Mol Ther, vol. 6(5):678-686, Nov. 2002.

Clement et al., Large-scale adeno-associated viral vector production using a herpesvirus-based system enables manufacturing for clinical studies, Hum Gene Therapy, vol. 20(8):796-806, Aug. 2009.

Davidoff et al., Purification of recombinant adeno-associated virus type 8 vectors by ion exchange chromatography generates clinical grade vector stock, J Virol Methods, vol. 121(2):209-215, Nov. 2004 (ePub Aug. 2004).

Feudner et al., Optimization of recombinant adeno-associated virus production using an herpes simplex virus aplicon system, Journal of Virological Methods, vol. 96(2):97-105, Aug. 2001.

Gao et al., Adeno-associated viruses undergo substantial evolution in primates during natural infections, Proc. Natl. Acad. Sci. U.S.A., vol. 100 (10):6081-6086, May 2003 (ePub Apr. 2003).

Gao et al, Clades of Adeno-Associated Viruses are Widely disseminated in Human Tissues, J. Virology, vol. 78(12):6381-6388, Jun. 2004.

GenBank Accession No. AAB95452, capsid protein VP1 [Adeno-associated virus 3B], Jan. 1998.

GenBank Accession No. AAD27758, nonstructural protein [Adeno-associated virus 1], Apr. 1999.

GenBank Accession No. AAO88201, capsid protein [Non-human primate Adeno-associated virus], May 2003.

GenBank Accession No. AAS99264, capsid protein VP1 [Adeno-associated virus 9], Jun. 2004.

GenBank Accession No. AAS99285, capsid protein VP1 [Adeno-associated virus], Jun. 2004.

GenBank Accession No. ACB55316, capsid protein VP1, partial (endogenous virus) [Adeno-associated virus], Jul. 2016.

GenBank Accession No. NP_043941, capsid protein [Adeno-associated virus-3], Aug. 2018.

GenBank Accession No. NP_049542, capsid protein [Adeno-associated virus-1], Aug. 2018.

GenBank Accession No. YP_068409, capsid protein [Adeno-associated virus-5], Aug. 2018.

GenBank Accession No. YP_077180, capsid protein [Adeno-associated virus-8], Aug. 2018.

GenBank Accession No. YP_680426, major coat protein VP1 [Adeno-associated virus-2], Aug. 2018.

Grimm et al., Titration of AAV-2 particles via a novel capsid ELISA: packaging of genomes can limit production of recombinant AAV-2, Gene Therapy, vol. 6(7): 1322-1330, Jul. 1999.

Gurda et al., Mapping a neutralizing epitope onto the capsid of adeno-associated virus serotype 8, Journal of Virology, vol. 86(15):7739-7751, August 2012 (ePub May 2012).

Gurda et al., Capsid antibodies to different adeno-associated virus serotypes bind common regions, Journal of Virology, vol. 87(16):9111-9124, Aug. 2013 (ePub Jun. 2013).

Halbert et al, Adeno-Associated Virus Type 6 (AAV6) Vectors Mediate Efficient Transduction of Airway Epithelial Cells in Mouse Lungs Compared to that of AAV2 Vectors, J. Virol., vol. 75(14):6615-6624, Jul. 2001.

Harbison et al., Examining the cross-reactivity and neutralization mechanisms of a panel of mAbs against adeno-associated virus serotypes 1 and 5, Journal of General Virology, vol. 93(Pt 2):347-355, Feb. 2012 (ePub Nov. 2011).

Hellström et al., Cellular tropism and transduction properties of seven adeno-associated viral vector serotypes in adult retina after intravitreal injection, Gene Ther, vol. 16(4):521-532, Apr. 2009 (ePub Dec. 2008).

Jenny et al., Evaluation of a serum-free medium for the production of rAAV-2 using HeLa derived producer cells, Cytotechnology, vol. 49:11-23, Sep. 2005.

Kaludov et al., Scalable purification of adeno-associated virus type 2, 4, or 5 using ion-exchange chromatography, Hum. Gene Therapy, vol. 13(10):1235-1243, Jul. 2002.

Kern et al, Identification of a Heparin-Binding Motif on Adeno-Associated Virus Type 2 Capsids, Journal of Virology, vol. 77(20):11072-11081, Oct. 2003.

Kotin et al., Large-scale recombinant adeno-associated virus production, Hu Mol Genet, vol. 20(1):R2-R6, Apr. 2011.

Lochrie et al, Mutations on the External Surfaces of Adeno-Associated Virus Type 2 Capsids that affect Transduction and Neutralization, Journal of Virology, vol. 80(2):821-834, Jan. 2006.

Lock et al., Absolute determination of single-stranded and self-complementary adeno-associated viral vector genome titers by droplet, digital PCR, Hu Gene Therapy Methods, vol. 25(2):115-25, Apr. 2014 (ePub Feb. 2014).

Lock et al., Rapid, Simple, and Versatile Manufacturing of Recombinant Adeno-Associated Viral Vectors at Scale, Hum Gene Ther, vol. 21(1):1259-1271, Oct. 2010.

Lock et al., Analysis of Particle Content of Recombinant Adeno-Associated Virus Serotype 8 Vectors by Ion-Exchange Chromatography, Human Gene Therapy Methods, vol. 23(1):56-64, Feb. 2012.

Mietzsch et al., OneBac: platform for scalable and high-titer production of adeno-associated virus serotype 1-12 vectors for gene therapy, Hum Gene Therapy, vol. 25(3):212-222, Mar. 2014 (Jan. 2014).

Mietzsch et al., OneBac 2.0: Sf9 Cell Lines for Production of AAV1, AAV2, and AAV8 Vectors with Minimal Encapsidation of Foreign

(56) References Cited

OTHER PUBLICATIONS

DNA. Hum Gene Ther Methods. Feb. 2017;28(1):15-22. doi: 10.1089/hgtb.2016.164. Published Online: Feb. 1, 2017.

Mietzsch et al., OneBac 2.0: Sf9 Cell Lines for Production of AAV5 Vectors with Enhanced Infectivity and Minimal Encapsidation of Foreign DNA. Hum Gene Ther. Oct. 2015;26(10):688-97, Published Online:Jul. 2, 2015.

Mingozzi et al., Overcoming preexisting humoral immunity to AAV using capsid decoys, Sci Transl med, vol. 5(194), Jul. 2013.

Moskalenko et al., Epitope mapping of human anti-adeno-associated virus type 2 neutralizing antibodies: implications for gene therapy and virus structure, Journal of Virology, vol. 74:1761-1766, Feb. 2000.

Müller et al, Improved Cardiac Gene Transfer by Transcriptional and Transductional Targeting of Adeno-Associated Viral Vectors, Cardiovascular Research, vol. 70(1):70-8, Apr. 2006 (E-published Jan. 31, 2006).

Nam et al., Structure of adeno-associated virus serotype 8, a gene therapy vector, J Virol, vol. 81:12260-12271, Nov. 2007 (Aug. 2007).

Nony et al. "Evidence for packaging of rep-cap sequences into adeno-associated virus (AAV) type 2 capsids in the absence of inverted terminal repeats: a model for generation of rep-positive AAV particles." Journal of virology 77.1 (2003): 776-781, (Jan. 2003).

Okada et al., 421. Large-Scale Production of AAV and Adenovirus Vectors Using Active Gassing with Large Culture Vessel, Molecular Therapy, vol. 9(S1):S161-S162, May 2004.

Okada et al., Scalable purification of adeno-associated virus serotype 1 (AAV1) and AAV8 vectors, using dual ion-exchange adsorptive membranes, Hum Gene Ther, vol. 20:1013-1021, Sep. 2009.

Opie et al, Identification of Amino Acid Residues in the Capsid Proteins of Adeno-Associated Virus Type 2 that Contribute to Heparan Sulfate Proteoglycan Binding, Journal of Virology, vol. 77(12):6995-7006, Jun. 2003.

Pettersen et al., UCSF Chimera—a visualization system for exploratory research and analysis, J Comput Chem, vol. 25:1605-1612, Oct. 2004.

Potter et al, A simplified purification protocol for recombinant adeno-associated virus vectors Molecular Therapy—Methods & Clinical Development, vol. 1:14034, Aug. 2014.

Qu et al, Separation of adeno-associated virus type 2 empty particles from genome containing vectors by anion-exchange col. chromatography, Journal of Virological Methods, vol. 140(1-2):183-192, Feb. 2007.

Sanner et al., Reduced surface: an efficient way to compute molecular surfaces, Biopolymers, vol. 38:305-320, Mar. 1996.

Sektrnik et al.. Poster: Chromatographic separation of full and empty AAV8 capsids, Mar. 2016, retrieved on Feb. 27, 2017 from http://ww.biaseparations.com/support/posters/product/download/file_id-2363.

Shen et al., Characterization of the relationship of AAV capsid domain swapping to liver transduction efficiency, Molecular Therapy, vol. 15:1955-1962, Nov. 2007 (ePub Aug. 2007).

Sommer et al., Quantification of adeno-associated virus particles and empty-capsids by optical density measurement, Molec. Ther, vol. 7:122-128, Jan. 2003.

Sonntag et al., A viral assembly factor promotes AAV2 capsid formation in the nucleolus, Proc Natl Acad Sci USA, vol. 107:10220-10225, Jun. 2010 (ePub May 2010).

Tenney et al., AAV8 capsid variable regions at the two-fold symmetry axis contribute to high liver transduction by mediating nuclear entry and capsid uncoating, Virology, vol. 454:227-236, Apr. 2014 (ePub Mar. 2014).

Thomas et al, Scalable recombinant adeno-associated virus production using recombinant herpes simplex virus type 1 coinfection of suspension-adapted mammalian cells, Hum Gene Ther, vol. 20:861-870, Aug. 2009.

Thomson et al., A comprehensive comparison of multiple sequence alignments, Nucl. Acids Res., vol. 27(13):2682-2690, Jul. 1999.

Urabe et al., Removal of empty capsids from type 1 adeno-associated virus vector stocks by anion-exchange transgene expression, Molecular Therapy, vol. 13(4):823-828, Apr. 2006 (ePub Feb. 2006).

Vandenberghe et al, Heparin Binding Directs Activation of T Cells Against Adeno-Associated Virus Serotype 2 Capsid, Nature Medicine, vol. 12(8): 967-971, Aug. 2006.

Vandenberghe et al., Efficient Serotype-Dependent Release of Functional Vector into the Culture Medium During Adeno-Associated Virus Manufacturing, Human Gene Therapy, vol. 21(10):1251-1257, Oct. 2010.

Virag et al., Producing recombinant adeno-associated virus in foster cells: overcoming production limitations using a baculovirus-insect cell expression strategy, Hu Gene Therapy, vol. 20:807-817, Aug. 2009.

Walsh et al, Parvovirus-Mediated Gene Transfer for the Haemophilias, Haemophilia, vol. 8(S2):60-67, Mar. 2002.

Wang et al., Identification of an adeno-associated virus binding epitope for AVB sepharose affinity resin, Molecular Therapy, vol. 2:15040, Jan. 2015.

Wobus et al., Monoclonal antibodies against the adeno-associated virus type 2 (AAV-2) capsid: epitope mapping and identification of capsid domains involved in AAV-2-cell interaction and neutralization of AAV-2 infection, Journal of Virology, vol. 74(19):9281-9293, Oct. 2000.

Wu et al, Single Amino Acid changes can Influence Titer, Heparin Binding, and Tissue Tropism in Different Adeno-Associated Virus Serotypes, Journal of Virology, vol. 80(22):11393-11397, Nov. 2006.

Ye et al., Herpes simplex virus clearance during purification of a recombinant adeno-associated virus serotype 1 vector, Hu Gene Ther Clin Dev, vol. 25:212-217, Dec. 2014.

Zolotukhin et al., Production and purification of serotype 1, 2, and 5 recombinant adeno-associated viral vectors, Methods, vol. 28(2):158-167, Jul. 2002.

QA—Strong AEX. Webpage accessed from https://www.biaseparations.com/en/products/monolithic-columns/products-for-preparative-applications/1/qa-strong-aex on Apr. 2, 2019, 4 pages.

Product Sheet & Instruction Manual. CIMac™ QA-0.1 Analytical Column (Quaternary amine) (Pores 1.3 µm), BIA Separations. Publication #:PSIM-110,5113-1,3-1903-FZE, pp. 1-9, 2019.

Product Information Sheet. POROS™ HQ and PI Perfusion Chromatography™ Columns for Anion Exchange Chromatography. Thermoscientific. pp. 1-6, Jul. 14, 2017.

Ion Exchange Chromatography. Webpage assessed from https://www.separations.eu.tosohbioscience.com/solutions/hplc-products/ion-exchange on May 2, 2019, 2 pages.

International Search Report and Written Opinion issued on International Patent Application No. PCT/US2016/066013, dated Mar. 13, 2017.

International Search Report and Written Opinion issued for International Patent Application No. PCT/US2016/065970, dated Sep. 18, 2017.

International Search Report and Written Opinion issued on International Patent Application No. PCT/US2016/065974, dated Mar. 13, 2017.

International Search Report and Written Opinion issued on International Patent Application No. PCT/US2016/065976, dated Mar. 9, 2017.

Communication pursuant to Article 94(3) EPC dated Mar. 29, 2019 in the European Application No. 16884241.7.

International Search Report and Written Opinion issued on related International Patent Application No. PCT/US2007/010055 (International Publication No. WO-2007/127264), dated Feb. 20, 2008.

Notice of Allowance issued on parent U.S. Appl. No. 14/919,801, dated Aug. 28, 2018.

Advisory Action issued on parent U.S. Appl. No. 14/919,801, dated Jun. 22, 2018.

Response to Final Office Action issued Jan. 16, 2018 on parent U.S. Appl. No. 14/919,801, dated Jun. 15, 2018.

Final Office Action issued on parent U.S. Appl. No. 14/919,801, dated Jan. 16, 2018.

(56) References Cited

OTHER PUBLICATIONS

Response to Non-Final Office Action issued Mar. 29, 2017 on parent U.S. Appl. No. 14/919,801, dated Sep. 27, 2017.
Non-Final Office Action issued on parent U.S. Appl. No. 14/919,801, dated Mar. 29, 2017.
Notice of Allowance issued on grandparent U.S. Appl. No. 12/226,588, dated Jul. 24, 2015.
Response to Final Office Action dated Jun. 4, 2015 on grandparent U.S. Appl. No. 12/226,588, dated Jul. 9, 2015.
Final Office Action issued on grandparent U.S. Appl. No. 12/226,588, dated Jun. 4, 2015.
Response to Non-Final Office Action dated Oct. 3, 2014 on grandparent U.S. Appl. No. 12/226,588, dated Feb. 3, 2015.
Non-Final Office Action issued on grandparent U.S. Appl. No. 12/226,588, dated Oct. 3, 2014.
Advisory Action issued on grandparent U.S. Appl. No. 12/226,588, dated Feb. 11, 2013.
Response to Final Office Action dated Nov. 2, 2012 on grandparent U.S. Appl. No. 12/226,588, dated Feb. 4, 2013.
Final Office Action issued on grandparent U.S. Appl. No. 12/226,588, dated Nov. 2, 2012.
Responses to Non-Final Office Action dated Dec. 22, 2011 on grandparent U.S. Appl. No. 12/226,588, dated Jun. 19, 2012, dated Jul. 2, 2012 and dated Jul. 16, 2012.
Non-Final Office Action issued on grandparent U.S. Appl. No. 12/226,588, dated Dec. 22, 2011.
Amendment submitted with Filing of RCE in response to Final Office Action dated Jul. 27, 2011 on grandparent U.S. Appl. No. 12/226,588, dated Nov. 11, 2011.
Final Office Action issued on grandparent U.S. Appl. No. 12/226,588, dated Jul. 27, 2011.
Responses to Non-Final Office Action dated Nov. 29, 2010 on grandparent U.S. Appl. No. 12/226,588, dated Feb. 28, 2011 and dated May 13, 2011.
Non-Final Office Action issued on grandparent U.S. Appl. No. 12/226,588, dated Nov. 29, 2010.
Response to Restriction Requirement dated Jul. 16, 2010 on grandparent U.S. Appl. No. 12/226,588, dated Aug. 31, 2010.
Restriction Requirement issued on grandparent U.S. Appl. No. 12/226,588, dated Jul. 16, 2010.
Decision to Grant issued on related European Patent Application No. 07756027.4, dated Nov. 22, 2012.
Response to Communication dated Apr. 11, 2011 for related European Patent Application No. 07756027.4, dated Jun. 13, 2011.
Communication issued on related European Patent Application No. 07756027.4, dated Apr. 11, 2011.
Response to Communication dated May 31, 2010 for related European Patent Application No. 07756027.4, dated Dec. 10, 2010.
Communication issued on related European Patent Application No. 07756027.4, dated May 31, 2010.
Response to Communication dated Apr. 24, 2009 issued on related European Patent Application No. 07756027.4, dated Nov. 3, 2009.
Communication issued on related European Patent Application No. 07756027.4, dated Apr. 24, 2009.
Notice of Grant issued on related Chinese Patent Application No. 200780014975.8, dated Jun. 4, 2013 with an unofficial translation provided by Agent.
Second Office Action issued on related Chinese Patent Application No. 200780014975.8, dated Dec. 20, 2012 with an unofficial translation provided by Agent.
First Office Action issued on related Chinese Patent Application No. 200780014975.8, dated Mar. 7, 2012 with an unofficial translation provided by Agent.
Final Office Action issued on related Japanese Patent Application No. 2009-507783, dated Nov. 6, 2012 with an unofficial translation provided by Agent.
Office Action issued on related Japanese Patent Application No. 2009-507783, dated Jun. 12, 2012 with an unofficial translation provided by Agent.
Office Action issued on related European Application No. 16825937.2, dated Sep. 12, 2019.
Office Action issued on related European Application No. 16884241.7, dated Mar. 29, 2019.
Response to Office Action dated Oct. 8, 2019 issued on related European Patent Application No. 16884241.7, dated Mar. 29, 2019.
Office action issued on related European Application No. EP16825937.2, dated Apr. 30, 2020.
Office action issued on counterpart European Application No. EP16822315.4, dated Apr. 30, 2020.
Office action issued on related European application No. EP16884241.7, dated Nov. 26, 2019.
Response to Office action dated Nov. 26, 2020 issued on related European Patent Application No. EP16884241.7, dated Jun. 8, 2020.
Office action issued on counterpart European application No. EP1688421.7, dated Aug. 7, 2020.
Final Office Action dated Jan. 8, 2021 issued on related U.S. Appl. No. 16/060,405.
Notice of Allowance dated Jan. 25, 2021 issued on related U.S. Appl. No. 16/060,406.
Notice of Allowance dated Jan. 15, 2021 issued on related U.S. Appl. No. 16/060,404.
Communication issued in related European Patent Application No. 16884241.7, dated Aug. 13, 2021.
Hordeaux et al., Efficient central nervous system AAVrh10-mediated intrathecal gene transfer in adult and neonate rats, Gene Therapy, vol. 22(4):316-324, Apr. 2015.
Giove et al., Transduction of the inner mouse retina using AAVrh8 and AAVrh10 via intravitreal injection, Experimental Eye Research, vol. 91 (5):652-659, Nov. 2010.
Thwaite et al., AAVrh. 10 immunogenicity 11 in mice and humans. Relevance of antibody cross-reactivity in human gene therapy, Gene Therapy, vol. 22(2):196-201, Nov. 2014.
Extended European Search Report dated Mar. 31, 2022 issued in corresponding European Patent Application No. 21188952.2.
Merten, "AAV vector production: state of the art developments and remaining challenges," Bioinsights: Cell & Gene therapy Insights, pp. 521-551, DOI: 10.18609/cgti.2016.067, Dec. 2016.
Blouin et al., "Improving rAAV production and purification: towards the definition of a scaleable process," The Journal of Gene Medicine, vol. 6:S223-S228, DOI: 10.1002/jgm.505, Feb. 2004.
IEX Textbook chapters (GE Healthcare, Ion Exchange Chromatography & Chromatofocusing: Principles and Methods, pp. 1-59, Jan. 2010.).
Qu et al., "Calcium-ion-modulated ceramic hydroxyapatite resin for the scalable purification of recombinant Adeno Associated Virus serotype 9," Journal of Chromatography B, vol. 990(2015):15-22, Mar. 2015.
ScienceDirect Topics, https://www.sciencedirect.com/topics/agricultural-and-biological-sciences/fast-protein-liquid-chromatography, retrieved Feb. 21, 2023.
Notice of Opposition Filed dated Nov. 11, 2022 issued in related European Patent Application No. 16884241.7.
Provisional U.S. Appl. No. 62/266,357, filed Dec. 11, 2015.
Provisional U.S. Appl. No. 62/322,071, filed Apr. 13, 2016.
Response to Communication issued pursuant to Art. 94(2) EPC issued on European Patent Application No. 16884241.7, dated Oct. 8, 2019.

FIG 2B

| Peak | VP3 band volume | total pt | Empty pt | GC | E:F | % empty |
|---|---|---|---|---|---|---|
| P1+ P3+ P4 | 553620 | 1.11E+10 | 9.79E+09 | 1.28E+09 | 8:1 | 88% |
| P2 | 621927 | 1.24E+10 | 0.00E+00 | 1.50E+10 | 0:1 | 0% |
| P5 | 870336 | 1.74E+10 | 1.73E+10 | 1.44E+08 | 120:1 | 99% |

| Peak | VP3 band volume | Total pt | Empty pt | GC | E:F | % Empty |
|---|---|---|---|---|---|---|
| P1 | 17010940 | 2.69E+10 | 1.84E+10 | 8.52E+09 | 2:1 | 68% |
| P2 | 3516826 | 4.43E+09 | 0.00E+00 | 9.8E+09 | 0:1 | 0% |
| P3/P4 | 5193120 | 7.23E+09 | 2.79E+09 | 4.44E+09 | 0.6:1 | 39% |
| P5 | 25083235 | 4.04E+10 | 3.88E+10 | 1.58E+09 | 25:1 | 96% |

FIG 3B

SEQUENCE LISTING

<160> NUMBER OF SEQ ID NOS: 1

<210> SEQ ID NO 1
<211> LENGTH: 738
<212> TYPE: PRT
<213> ORGANISM: Artificial Sequence
<220> FEATURE:
<223> OTHER INFORMATION: Adeno-associated virus 8 vp1 capsid protein

<400> SEQUENCE: 1

Met Ala Ala Asp Gly Tyr Leu Pro Asp Trp Leu Glu Asp Asn Leu Ser
1               5                   10                  15

Glu Gly Ile Arg Glu Trp Trp Ala Leu Lys Pro Gly Ala Pro Lys Pro
            20                  25                  30

Lys Ala Asn Gln Gln Lys Gln Asp Asp Gly Arg Gly Leu Val Leu Pro
        35                  40                  45

Gly Tyr Lys Tyr Leu Gly Pro Phe Asn Gly Leu Asp Lys Gly Glu Pro
    50                  55                  60

Val Asn Ala Ala Asp Ala Ala Ala Leu Glu His Asp Lys Ala Tyr Asp
65                  70                  75                  80

Gln Gln Leu Gln Ala Gly Asp Asn Pro Tyr Leu Arg Tyr Asn His Ala
                85                  90                  95

Asp Ala Glu Phe Gln Glu Arg Leu Gln Glu Asp Thr Ser Phe Gly Gly
            100                 105                 110

Asn Leu Gly Arg Ala Val Phe Gln Ala Lys Lys Arg Val Leu Glu Pro
        115                 120                 125

Leu Gly Leu Val Glu Glu Gly Ala Lys Thr Ala Pro Gly Lys Lys Arg
    130                 135                 140

Pro Val Glu Pro Ser Pro Gln Arg Ser Pro Asp Ser Ser Thr Gly Ile
145                 150                 155                 160

Gly Lys Lys Gly Gln Gln Pro Ala Arg Lys Arg Leu Asn Phe Gly Gln
                165                 170                 175

Thr Gly Asp Ser Glu Ser Val Pro Asp Pro Gln Pro Leu Gly Glu Pro
            180                 185                 190

Pro Ala Ala Pro Ser Gly Val Gly Pro Asn Thr Met Ala Ala Gly Gly
        195                 200                 205

Gly Ala Pro Met Ala Asp Asn Asn Glu Gly Ala Asp Gly Val Gly Ser
    210                 215                 220

Ser Ser Gly Asn Trp His Cys Asp Ser Thr Trp Leu Gly Asp Arg Val
225                 230                 235                 240

Ile Thr Thr Ser Thr Arg Thr Trp Ala Leu Pro Thr Tyr Asn Asn His
                245                 250                 255

Leu Tyr Lys Gln Ile Ser Asn Gly Thr Ser Gly Gly Ala Thr Asn Asp
            260                 265                 270

Asn Thr Tyr Phe Gly Tyr Ser Thr Pro Trp Gly Tyr Phe Asp Phe Asn
        275                 280                 285

Arg Phe His Cys His Phe Ser Pro Arg Asp Trp Gln Arg Leu Ile Asn
    290                 295                 300

Asn Asn Trp Gly Phe Arg Pro Lys Arg Leu Ser Phe Lys Leu Phe Asn
305                 310                 315                 320

Ile Gln Val Lys Glu Val Thr Gln Asn Glu Gly Thr Lys Thr Ile Ala
                325                 330                 335

Asn Asn Leu Thr Ser Thr Ile Gln Val Phe Thr Asp Ser Glu Tyr Gln
            340                 345                 350

Leu Pro Tyr Val Leu Gly Ser Ala His Gln Gly Cys Leu Pro Pro Phe

```
             355                 360                 365
     Pro Ala Asp Val Phe Met Ile Pro Gln Tyr Gly Tyr Leu Thr Leu Asn
     370                 375                 380

Asn Gly Ser Gln Ala Val Gly Arg Ser Ser Phe Tyr Cys Leu Glu Tyr
 385                 390                 395                 400

Phe Pro Ser Gln Met Leu Arg Thr Gly Asn Asn Phe Gln Phe Thr Tyr
                     405                 410                 415

Thr Phe Glu Asp Val Pro Phe His Ser Ser Tyr Ala His Ser Gln Ser
                 420                 425                 430

Leu Asp Arg Leu Met Asn Pro Leu Ile Asp Gln Tyr Leu Tyr Tyr Leu
             435                 440                 445

Ser Arg Thr Gln Thr Thr Gly Gly Thr Ala Asn Thr Gln Thr Leu Gly
         450                 455                 460

Phe Ser Gln Gly Gly Pro Asn Thr Met Ala Asn Gln Ala Lys Asn Trp
 465                 470                 475                 480

Leu Pro Gly Pro Cys Tyr Arg Gln Gln Arg Val Ser Thr Thr Thr Gly
                     485                 490                 495

Gln Asn Asn Asn Ser Asn Phe Ala Trp Thr Ala Gly Thr Lys Tyr His
                 500                 505                 510

Leu Asn Gly Arg Asn Ser Leu Ala Asn Pro Gly Ile Ala Met Ala Thr
             515                 520                 525

His Lys Asp Asp Glu Glu Arg Phe Phe Pro Ser Asn Gly Ile Leu Ile
         530                 535                 540

Phe Gly Lys Gln Asn Ala Ala Arg Asp Asn Ala Asp Tyr Ser Asp Val
 545                 550                 555                 560

Met Leu Thr Ser Glu Glu Ile Lys Thr Thr Asn Pro Val Ala Thr
                     565                 570                 575

Glu Glu Tyr Gly Ile Val Ala Asp Asn Leu Gln Gln Gln Asn Thr Ala
                 580                 585                 590

Pro Gln Ile Gly Thr Val Asn Ser Gln Gly Ala Leu Pro Gly Met Val
             595                 600                 605

Trp Gln Asn Arg Asp Val Tyr Leu Gln Gly Pro Ile Trp Ala Lys Ile
         610                 615                 620

Pro His Thr Asp Gly Asn Phe His Pro Ser Pro Leu Met Gly Gly Phe
 625                 630                 635                 640

Gly Leu Lys His Pro Pro Pro Gln Ile Leu Ile Lys Asn Thr Pro Val
                     645                 650                 655

Pro Ala Asp Pro Pro Thr Thr Phe Asn Gln Ser Lys Leu Asn Ser Phe
                 660                 665                 670

Ile Thr Gln Tyr Ser Thr Gly Gln Val Ser Val Glu Ile Glu Trp Glu
             675                 680                 685

Leu Gln Lys Glu Asn Ser Lys Arg Trp Asn Pro Glu Ile Gln Tyr Thr
         690                 695                 700

Ser Asn Tyr Tyr Lys Ser Thr Ser Val Asp Phe Ala Val Asn Thr Glu
 705                 710                 715                 720

Gly Val Tyr Ser Glu Pro Arg Pro Ile Gly Thr Arg Tyr Leu Thr Arg
                     725                 730                 735

Asn Leu
```

SCALABLE PURIFICATION METHOD FOR AAV8

CROSS-REFERENCE TO RELATED APPLICATIONS

This is a continuation of U.S. patent application Ser. No. 16/060,408, filed Jun. 7, 2018, which is a National Stage Entry under 35 U.S.C. 371 of International Patent Application No. PCT/US2016/065976, filed Dec. 9, 2016, which claims the benefit of U.S. Provisional Patent Application No. 62/266,341, filed Dec. 11, 2015, and U.S. Provisional Patent Application No. 62/322,098, filed Apr. 13, 2016. These applications are incorporated by reference herein.

STATEMENT REGARDING FEDERALLY SPONSORED RESEARCH OR DEVELOPMENT

This invention was made with government support under P01 HL059407 awarded by the National Institutes of Health (NIH). The US government has certain rights in the invention.

BACKGROUND OF THE INVENTION

This invention describes a novel scalable method for producing rAAV suitable for clinical applications.

The use of recombinant adeno-associated viruses (rAAV) for a variety of gene therapy and vaccine approaches has been described. However, even with these approaches, scalable methods for purification of rAAV have been lacking.

Adeno-associated virus (AAV), a member of the Parvovirus family, is a small, non-enveloped virus. AAV particles comprise an AAV capsid composed of 60 capsid protein subunits, VP1, VP2 and VP3, which enclose a single-stranded DNA genome of about 4.7 kilobases (kb). These VP1, VP2 and VP3 proteins are present in a predicted ratio of about 1:1:10, and are arranged in an icosahedral symmetry. Individual particles package only one DNA molecule strand, but this may be either the plus or minus strand. Particles containing either strand are infectious. AAV is assigned to the genus, *Dependovirus*, because the virus was discovered as a contaminant in purified adenovirus stocks. AAV's life cycle includes a latent phase and an infectious phase. Replication occurs by conversion of the linear single stranded DNA genome to a duplex form, and subsequent amplification, from which progeny single strands are rescued, replicated, and packaged into capsids in the presence of helper functions. The properties of non-pathogenicity, broad host range of infectivity, including non-dividing cells, and integration make AAV an attractive delivery vehicle.

Recombinant AAV particles are produced in permissive (packaging) host cell cultures and co-expression of helper virus AAV rep and AAV cap genes are required, for replication and packaging, the recombinant genome into the viral particle. Genes necessary for genome replication, capsid formation and genome packaging can be expressed from transfected plasmids, integrated into the host cell genome or introduced to the cell by recombinant viruses. Typically, cells are lysed to release rAAV particles and maximize yield of recovered rAAV. However, the cell lysate contains various cellular components such as host cell DNA, host cell proteins, media components, and in some instances, helper virus or helper virus plasmid DNA, which must be separated from the rAAV vector before it is suitable for in vivo use. Recent advances in rAAV production include the use of non-adherent cell suspension processes in stirred tank bioreactors and production conditions whereby rAAV vectors are released into the media or supernatant reducing the concentration of host cellular components present in the production material but still containing appreciable amounts of in-process impurities. See U.S. Pat. No. 6,566,118 and PCT WO 99/11764. Therefore, rAAV particles may be collected from the media and/or cell lysate and further purified.

Certain previously described purification methods for rAAV are not scalable and/or not adaptable to good manufacturing practices, including, e.g., cesium chloride gradient centrifugation and iodixanol gradient separation. See, e.g., M. Potter et al, Molecular Therapy—Methods & Clinical Development (2014), 1: 14034, pp 1-8.

US Patent Publication No. 2005/0024467 reports that rAAV capsid serotypes such as rAAV-1, 4, 5, and 8 bind weakly to anionic resins either as purified virus stock or in the presence of in-process production impurities such as host cell DNA, host cell proteins, serum albumin, media components, and helper virus components. Purification of those capsid serotypes is described as involving anion-exchange chromatography in combination with other purification methods, such as iodixinol density-gradient centrifugation. See, e.g., Zolotukhin et al., Methods 28(2):158-167 (2002) and Kaludov et al., Hum. Gene Therapy 13:1235-1243 (2002); and U.S. Patent Publication No. 2004/0110266 A1. However, those methods are not readily scalable to commercial scale processes.

Other examples of one- or two-step ion-exchange chromatography purification have been reported for rAAV serotypes 1, 2, 4, 5, and 8. [Brument, N, et al. (2002). Mol Ther 6: 678-686; Okada, T, et al. (2009). Hum Gene Ther 20: 1013-1021; Kaludov, N, et al (2002). Hum Gene Ther 13: 1235-1243; Zolotukhin, S, et al. (2002). Methods 28: 158-167; Davidoff, A M, et al. (2004). J Virol Methods 121: 209-215]. More recently, an affinity media incorporating an anti-AAV VHH ligand, a single-domain camelid antibody derivative, was described as being useful to purify serotypes 1, 2, 3, and 5. [Hellström, M, et al. (2009) Gene Ther 16: 521-532]. This affinity capture method focuses on purifying rAAV vectors from in-process production components of the cell culture including helper virus, as well as helper virus proteins, cellular proteins, host cell DNA, and media components present in the rAAV production stock. The affinity capture method described for purifying rAAV 1, 2, 3 and 5 particles is designed to purify rAAV from host cell and helper virus contaminants, but not to separate AAV particles from empty AAV capsids lacking packaged genomic sequences. Further, it is not clear from the literature that this separation is desirable. See, e.g., F. Mingozzi et al, Sci Transl med. 2013 Jul. 17: 5(194), avail in PMC 2014 Jul. 14, which suggests it may be desirable to include empty capsids as decoys which can be used to overcome preexisting humoral immunity to AAV can be overcome using capsid decoys. However, other authors have reported increase efficacy in rAAV1 vectors when they were separated from empty AAV1 capsids. See, e.g., M. Urabe et al, Molecular Therapy, 13(4):823-828 (April 2006).

There remains a need for scalable methods for separating pharmacologically active (full) rAAV particles having the desired transgene packaged from rAAV capsids which lack the desired transgene.

SUMMARY OF THE INVENTION

The present invention provides, inter alia, a scalable method for efficiently separating genome-containing AAV8 vector particles (full) from genome-deficient rAAV8 intermediates (empty capsids). Also provided are purified AAV8 vector particles.

In one aspect, the method for separating full AAV8 viral particles from empty AAV8 intermediates comprises subjecting a mixture comprising recombinant AAV8 viral particles and AAV8 vector intermediates/byproducts to fast performance liquid chromatography (FPLC), wherein the AAV8 viral particles and AAV8 intermediates are bound to a strong anion exchange resin equilibrated at a pH of about 10.2 and subjected to a salt gradient while monitoring the eluate for ultraviolet absorbance at about 260 nm and about 280 nm. The AAV8 full capsids are collected from a fraction which is eluted when the ratio of A260/A280 reaches an inflection point. More particularly, the full capsids are collected from the eluted fraction(s) characterized by having a higher peak (area under the curve) at an absorbance of 260 nm as compared to the peak (area under the curve) at an absorbance of 280 nm. The majority of the fractions observed for the process disclosed herein have a higher amount of empty capsids (higher peak/area under curve at A280). The absorbance peak at 260 nm being equal to or exceeding the absorbance peak at 280 nm is indicative of the fraction containing the full capsids.

In a further aspect, the sample loaded into the FPLC method contains full recombinant AAV8 viral particles and AAV8 intermediates (empty capsids) that had been purified from production system contaminants using affinity capture. In one embodiment, the affinity capture is performed using a high performance affinity resin having an antibody specific for AAV.

In still another aspect, disclosed herein is a scalable method for separating full AAV8 viral particles from AAV8 intermediates by using an anti-AAV antibody based affinity capture resin followed by an anion exchange resin. In one embodiment, the mixture containing the AAV8 viral particles and AAV8 intermediates is loaded onto the affinity resin in a buffer having a high salt concentrations, e.g., about 400 nM NaCl to about 650 mM NaCl or another salt(s) having an equivalent ionic strength. The wash step for the affinity resin is thereafter performed at an even higher salt concentration, e.g., in the range of about 750 mM to about 1 M NacCl or equivalent. In one embodiment, the AAV8 mixture is maintained at a salt concentration of about 400 mM NaCl to about 650 mM NaCl, or equivalent prior to being applied to the anion exchange resin column. In a further embodiment, the rAAV8 mixture is maintained at this salt concentration following concentration and prior to loading onto the affinity resin.

In yet another aspect, a method for separating AAV8 viral particles from AAV8 capsid intermediates is provided, said method comprising: (a) mixing a suspension comprising recombinant AAV8 viral particles and AAV8 vector intermediates and a Buffer A comprising 20 mM to 50 mM Bis-Tris propane (BTP) and a pH of about 10.2 (e.g., 10.2); (b) loading the suspension of (a) onto a strong anion exchange resin column; (c) washing the loaded anion exchange resin with Buffer 1% B which comprises a salt having the ionic strength of 10 mM to 40 mM NaCl and BTP with a pH of about 10.2 (e.g., 10.2); (d) applying an increasing salt concentration gradient to the loaded and washed anion exchange resin, wherein the salt gradient is the equivalent of 10 mM to about 40 mM NaCl; and (e) collecting rAAV8 particles from the eluate obtained at a salt concentration equivalent to at least 70 mM NaCl, where the rAAV8 particles are at least about 90% purified from AAV8 intermediates.

In a further aspect, a scalable method is provided for separating pharmacologically active recombinant AAV8 viral particles containing DNA genomic sequences from inert genome-deficient (empty) AAV8 vector intermediates, said method comprising: (a) forming a loading suspension comprising: recombinant AAV8 viral particles and empty AAV8 capsid which have been purified to remove contaminants from an AAV producer cell culture in which the particles and intermediates were generated; and a Buffer A comprising 20 mM Bis-Tris propane (BTP) and a pH of about 10; (b) loading the suspension of (a) onto a strong anion exchange resin, said resin being in a vessel having an inlet for flow of a suspension and/or solution and an outlet permitting flow of eluate from the vessel; (c) washing the loaded anion exchange resin with Buffer 1% B which comprises 10 mM NaCl and 20 mM BTP with a pH of about 10.2; (d) applying an increasing salt concentration gradient to the loaded and washed anion exchange resin, wherein the salt gradient ranges from 10 mM to about 190 mM NaCl, inclusive of the endpoints, or an equivalent; and (e) collecting the rAAV particles from eluate collected following a salt concentration of at least about 70 mM NaCl, or an equivalent salt or ionic strength, said rAAV particles being purified away from AAV8 intermediates.

In a further aspect, the affinity resin separation comprises: (i) equilibrating the affinity resin with Buffer A1 which comprises about 200 mM to about 600 mM NaCl, about 20 mM Tris-Cl and a neutral pH prior to applying the material to the affinity resin; (ii) washing the loaded resin of (a) with Buffer C1 which comprises about 800 mM NaCl to about 1200 mM NaCl, 20 mM Tris-Cl and a neutral pH; (iii) washing the Buffer C1-washed resin of (b) with Buffer A1 to reduce salt concentration; (iv) washing the affinity resin of (c) with Buffer B which comprises about 200 nM to about 600 nM NaCl, 20 mM Sodium Citrate, pH about 2.4 to about 3; and (v) collecting the eluate of (iv) which comprises the full AAV8 particles and the empty AAV8 capsid fraction for loading onto the anion exchange resin.

In still another aspect, vector preparations are provided that have less than 5% contamination with AAV intermediates (including AAV empty capsids). In another aspect, vector preparations are provided that have less than 2% contamination with AAV empty capsids, or less than 1% contamination with AAV empty capsids. In a further aspect, AAV compositions are provided which are substantially free of AAV empty capsids.

Still other advantages of the present invention will be apparent from the detailed description of the invention.

BRIEF DESCRIPTION OF THE DRAWINGS

FIGS. 2A-2B show purification of an affinity purified self-complimentary AAV8 vector preparation by anion exchange chromatography on a monolith AEX column. FIG. 2A shows the chromatogram from a PorosAAV8™ affinity-purified AAV8 vector preparation ($3.8 \times 10^{13}$ GC) with a self-complimentary genome was run on an 8 mL CIMmultus QA™ column and the chromatogram is shown. The run was performed with 20 mM Bis-Tris-Propane (BTP) pH10.2 as the loading buffer (buffer A) and 20 mM BTP pH10.2-1M NaCl as the column strip buffer (Buffer B). A 60 CV linear salt gradient from 1-19% Buffer B was used to elute vector and the column was stripped with 100% Buffer B. The column was loaded 10 mL/min and thereafter the flow rate was maintained at 20 mL/min. A260 (line extending highest at peak P2 and second highest at peak P1, P3, P4 and P5), A280 (line extending highest at peak P1, P3, P4 and P5 and second highest at peak P2), programmed conductivity (polyline extending from y axis and connecting at ~-10 mAU) and actual conductivity (smooth line extending from y axis and connecting at ~-5 mAU) profiles are shown. Absorbance (mAU) is shown on the y axis. Run volume (mL) is shown as solid line beneath the x axis while buffer is indicated on the x axis above the run volume. The major peaks (labelled P1-P5) are indicated. FIG. 2B shows SDS PAGE-based particle quantification of peaks P1-P5. SDS PAGE gels were loaded with serial dilutions of an iodixanol gradient-purified "full" reference standard alongside f peak fractions. The capsid protein VP3 band was quantified for each dilution and a standard curve of particle number loaded versus band volume obtained. Peak fractions loaded to the gel were adjusted to the limits of the standard curve and article (pt) numbers determined for each by comparison of band volumes to the standard curve. pt: GC ratios and percent empty capsids for the peaks were derived by comparison of GC loaded and the determined pt number.

FIGS. 3A and 3B show the reproducibility of chromatogram peak distribution and A260/280 ratios for an affinity purified AAV8 vector preparation run at increased scale on a monolith AEX column. FIG. 3A shows the chromatogram from a PorosAAV8™ affinity-purified AAV8 vector preparation ($2.1 \times 10^{15}$ GC) with a single-stranded genome was run on an 8 mL CIMmultus QA™ column. The run was performed as described in the legend to FIG. 2. A260 (line extending highest at peak P2 and second highest at peak P1, P3, P4 and P5), A280 (line extending highest at peak P1, P3, P4 and P5 and second highest at peak P2), programmed conductivity (polyline extending from y axis and connecting at ~27 mAU) and actual conductivity (smooth line extending from y axis and connecting at ~32 mAU) profiles are shown. Absorbance (mAU) is shown on the y axis. Run volume (mL) is shown as solid line beneath the x axis while buffer is indicated on the x axis above the run volume. The major peaks (labelled P1-P5) are indicated. FIG. 3B shows SDS PAGE-based particle quantification of peaks P1-P5 was performed as described in the legend to FIG. 2.

DETAILED DESCRIPTION OF THE INVENTION

Figure 1:
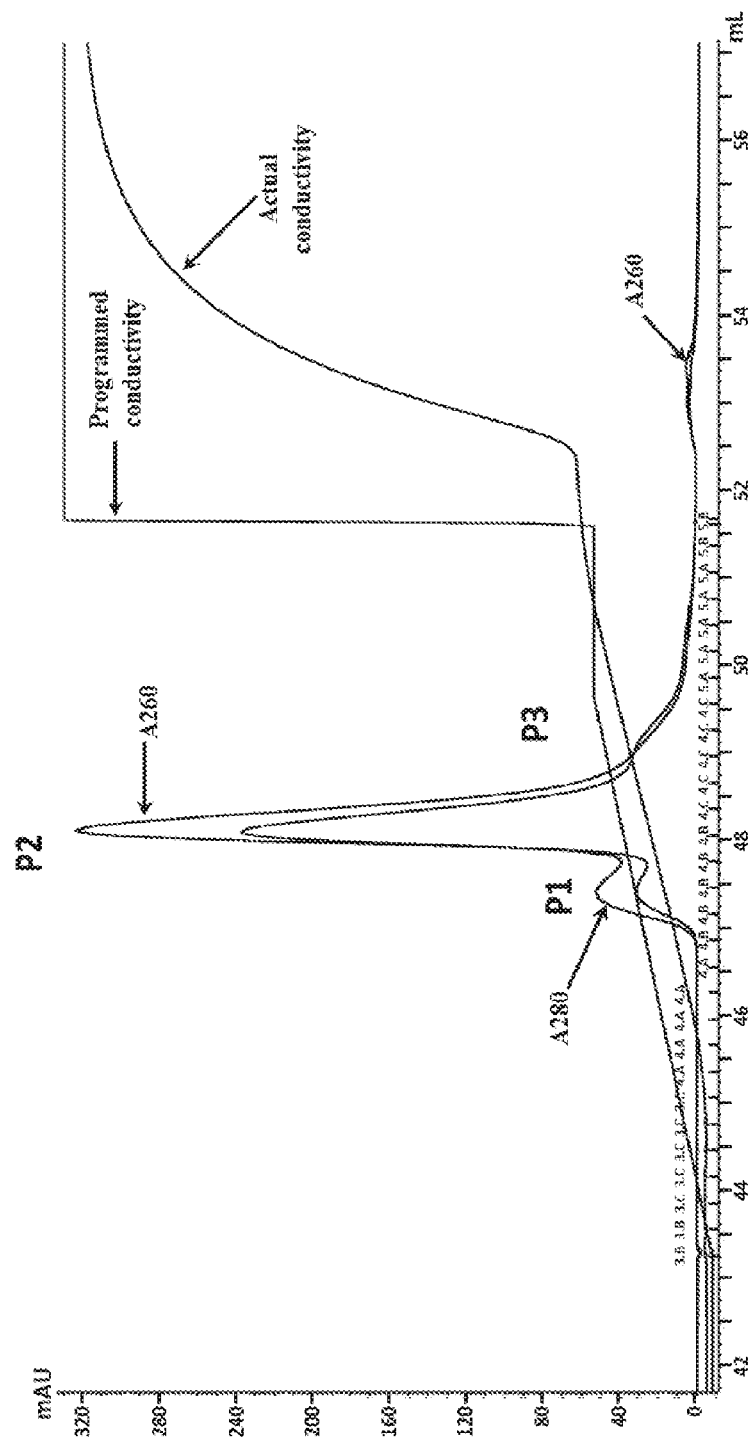
FIG. 1 shows separation of AAV8 vector particle populations on anion exchange resin (AEX) monolith column. A PorosAAV8™ affinity-purified AAV8 vector preparation ($8\times10^{13}$ GC) with a single-stranded genome was run on a 0.1 mL CIMac QA™ column and the chromatogram is shown. The run was performed with 20 mM Bis-Tris-Propane (BTP) pH10.0 as the loading buffer (buffer A) and 20 mM BTP pH10.2-1M NaCl as the column strip buffer (Buffer B). A 60 column volume (CV) linear salt gradient from 1-19% Buffer B was used to elute vector and the column was stripped with 100% Buffer B. The flow rate was maintained at 2 mL/min throughout the run. A260 (line extending second highest at peak P1 and highest at peak P2), A280 (line extending highest at peak P1 and second highest at peak P2), programmed conductivity (polyline extending from y axis and connecting at ~−2 mAU) and actual conductivity (smooth line extending from y axis and connecting at ~-5 mAU) profiles are shown. Absorbance (mAU) is shown on the y axis. Run volume (mL) is shown as solid line beneath the x axis while buffer is indicated on the x axis above the run volume. The major peaks (labelled P1-P3) are indicated.

A scalable technology for production of purified rAAV8 for use in a variety of gene transfer and/or other applications is provided herein. Suitably, the method purifies rAAV8 viral particles from production culture contaminants such as helper virus, helper virus proteins, plasmids, cellular proteins and DNA, media components, serum proteins, AAV rep proteins, unassembled AAV VP1, AAV VP2 and AAV VP3 proteins, and the like. Further, the method is particularly well suited for separating full rAAV8 viral particles from rAAV intermediates.

In one aspect, the method for separating full AAV8 viral particles from empty AAV8 intermediates comprises subjecting a mixture comprising recombinant AAV8 viral particles and AAV8 vector intermediates to fast performance liquid chromatography, wherein the AAV8 viral particles and AAV8 intermediates are bound to a strong anion exchange resin equilibrated at a pH of about 10.2 (e.g., 10.0 to 10.4, preferably 10.2) and subjected to a salt gradient while monitoring eluate for ultraviolet absorbance at about 260 nm and about 280 nm, respectively.

More particularly, the presence of AAV8 capsids having genomic sequences packaged therein ("full") and 26/280 absorbance ratios less than 1 is characteristic of AAV8 intermediates as defined herein. In general, the production cell culture may yield a mixture of rAAV8 "full" and rAAV8 "empty" or other intermediates in which 50% or greater are intermediates (including empties), at least 60% are intermediates, or greater than 70% are intermediates. In other embodiments, more or less of the genome copies are "empty"; as a consequence, a corresponding amount of eluted fractions are characterized by having 280 nm peaks (and corresponding larger areas under the curve which are larger than 260 nm peaks). Fractions characterized by peaks (and corresponding larger areas under the curve) at an absorbence of about 260 nm (A260) that are higher than the corresponding peaks at 260 nm (A260/A280 ratio is >1) are highly enriched in full rAAV8 particles. The AAV8 full capsids are collected from a fraction which is eluted when the peak for A260 crosses over and exceeds the peak for A280 (i.e., reaches an inflection point).

As used herein, "recombinant AAV8 viral particle" refers to nuclease-resistant particle (NRP) which has an AAV8 capsid, the capsid having packaged therein a heterologous nucleic acid molecule comprising an expression cassette for a desired gene product. Such an expression cassette typically contains an AAV 5' and/or 3' inverted terminal repeat sequence flanking a gene sequence, in which the gene sequence is operably linked to expression control sequences. These and other suitable elements of the expression cassette are described in more detail below and may alternatively be referred to herein as the transgene genomic sequences. This may also be referred to as a "full" AAV capsid. Such a rAAV viral particle is termed "pharmacologically active" when it delivers the transgene to a host cell which is capable of expressing the desired gene product carried by the expression cassette.

In many instances, rAAV particles are referred to as DNase resistant (DRP). However, in addition to this endonuclease (DNase), exonucleases may also be used in the purification steps described herein, to remove contaminating nucleic acids. Such nucleases may be selected to degrade single stranded DNA and/or double-stranded DNA, and RNA. Such steps may contain a single nuclease, or mixtures of nucleases directed to different targets, and may be endonucleases or exonucleases.

The term "nuclease-resistant" indicates that the AAV capsid has fully assembled around the expression cassette which is designed to deliver a transgene to a host cell and protects these packaged genomic sequences from degradation (digestion) during nuclease incubation steps designed to remove contaminating nucleic acids which may be present from the production process.

As used herein, "AAV8 capsid" refers to the AAV8 capsid having the encoded amino acid sequence of GenBank accession: YP_077180, which is incorporated by reference herein and reproduced in SEQ ID NO: 1. In addition, the methods provided herein can be used to purify other AAV having a capsid highly related to the AAV8 capsid. For example, AAV having about 99% identity to the referenced AAV8 capsid amino acid sequence in GenBank accession: YP_077180; U.S. Pat. Nos. 7,282,199; 7,790,449; 8,319,480; 8,962,330; 8,962,332, (i.e., less than about 1% variation from the referenced sequence), provided that the integrity of the ligand-binding site for the affinity capture purification is maintained and the change in sequences does not substantially alter the pH range for the capsid for the ion exchange resin purification. In another embodiment, the AAV8 capsid may have the VP1 sequence of the AAV8 variant described in WO2014/124282 or the dj sequence described in US 2013/0059732 A1 or U.S. Pat. No. 7,588,772 B2, which are incorporated by reference herein. Methods of generating the capsid, coding sequences therefore, and methods for production of rAAV viral vectors have been described. See, e.g., Gao, et al, Proc. Natl. Acad. Sci. U.S.A. 100 (10), 6081-6086 (2003), US 2013/0045186A1, and WO 2014/124282.

The term "identity" or "percent sequence identity" may be readily determined for amino acid sequences, over the full-length of a protein, a subunit, or a fragment thereof. Suitably, a fragment is at least about 8 amino acids in length, and may be up to about 700 amino acids. Examples of suitable fragments are described herein. Generally, when referring to "identity", "homology", or "similarity" between two different adeno-associated viruses, "identity", "homology" or "similarity" is determined in reference to "aligned" sequences. "Aligned" sequences or "alignments" refer to multiple nucleic acid sequences or protein (amino acids) sequences, often containing corrections for missing or additional bases or amino acids as compared to a reference sequence. Alignments are performed using a variety of publicly or commercially available Multiple Sequence Alignment Programs. Examples of such programs include, "Clustal W", "CAP Sequence Assembly", "MAP", and "MEME", which are accessible through Web Servers on the internet. Other sources for such programs are known to those of skill in the art. Alternatively, Vector NTI utilities are also used. There are also a number of algorithms known in the art that can be used to measure nucleotide sequence identity, including those contained in the programs described above. As another example, polynucleotide sequences can be compared using Fasta™, a program in GCG Version 6.1. Fasta™ provides alignments and percent sequence identity of the regions of the best overlap between the query and search sequences. For instance, percent sequence identity between nucleic acid sequences can be determined using Fasta™ with its default parameters (a word size of 6 and the NOPAM factor for the scoring matrix) as provided in GCG Version 6.1, herein incorporated by reference. Multiple sequence alignment programs are also available for amino acid sequences, e.g., the "Clustal X", "MAP", "PIMA", "MSA", "BLOCKMAKER", "MEME", and "Match-Box" programs. Generally, any of these programs are used at default settings, although one of skill in the art can alter these settings as needed. Alternatively, one of skill in the art can utilize another algorithm or computer program which provides at least the level of identity or alignment as that provided by the referenced algorithms and programs. See, e.g., J. D. Thomson et al, Nucl. Acids Res., "A comprehensive comparison of multiple sequence alignments", 27(13):2682-2690 (1999).

As used herein the term "AAV8 intermediate" or "AAV8 vector intermediate" refers to an assembled rAAV capsid which lacks genomic sequences packaged therein. These may also be termed an "empty" capsid. Such a capsid may contain no detectable genomic sequences of an expression cassette, or only partially packaged genomic sequences which are insufficient to achieve expression of the gene product. These empty capsids are non-functional to transfer the gene of interest to a host cell.

In one aspect, a method for separating rAAV8 particles having packaged genomic sequences from genome-deficient AAV8 intermediates is provided. This method involves subjecting a suspension comprising recombinant AAV8 viral particles and AAV8 capsid intermediates to fast performance liquid chromatography, wherein the AAV8 viral particles and AAV8 intermediates are bound to a strong anion exchange resin equilibrated at a pH of 10.2, and subjected to a salt gradient while monitoring eluate for ultraviolet absorbance at about 260 and about 280. Although less optimal for rAAV8, the pH may be in the range of about 10.0 to 10.4. In this method, the AAV8 full capsids are collected from a fraction which is eluted when the ratio of A260/A280 reaches an inflection point.

Fast protein liquid chromatography (FPLC), is a form of liquid chromatography that is often used to analyze or purify mixtures of proteins. As in other forms of chromatography, separation is possible because the different components of a mixture have different affinities for two materials, a moving fluid (the "mobile phase") and a porous solid (the stationary phase). In the present method, the mobile phase is an aqueous solution, or "buffer". The buffer flow rate may be controlled by gravity or a pump (e.g., a positive-displacement pump) and can be kept constant or varied. Suitably, the composition of the buffer can be varied by drawing fluids in different proportions from two or more external reservoirs. The stationary phase described herein is a strong anion exchange resin, typically composed of beads. These beads may be packed into a vessel, e.g., a cylindrical glass or plastic column, or another suitable vessel. As provided herein, volumes of the mobile phase are described as "column volumes". These volumes may be extrapolated to other vessel shapes and designs.

The eluate from the anion exchange resin column or other vessel is monitored for ultraviolet absorbance at about 260 nm and 280 nm. As provided herein, "full" AAV8 capsids are characterized by having a UV absorbance of about 260 nm, whereas as "empty" capsids are characterized by having a UV absorbance of about 280 nm. Typically, the majority of the eluate fractions contain empty capsids and as the salt gradient progresses, the majority of the eluate is characterized by a curve for A280 exceeding that of A260. By monitoring UV absorbance for when the eluate is characterized by the curve for A260 crossing over the curve for A280 (ratio of A260/A280 greater than 1), one can selectively collect the "full capsids" until such time as the ratio reverts to A280/A260 greater than 1.

In one embodiment, this fraction(s) selectively collected at the inversion point is characterized by having the total collected rAAV contain at least about 90% "full capsids", and preferably, at least 95% "full capsids". In a further embodiment, these fractions may be characterized by having a ratio of "intermediate" to "full" less than 0.75, more preferably 0.5, preferably less than 0.3.

As used herein, an "anion exchange resin" refers to an insoluble matrix or solid support (e.g., beads) capable of having a surface ionization over a pH range of about 1 to about 14. In one embodiment, a strong anion exchange resin is a solid support having a surface coated with quaternized polyethyleneimine. An example of such a strong anionic exchange resin is the solid support of the CIMultus QA™ column. For example, the anion exchange resin may be a quaternary amine ion exchange resin. In a further embodiment, the anion exchange resin comprises trimethylamine and a support matrix comprising poly(glycidyl methacrylate-co-ethylene dimethacrylate). However, other suitable anion exchange resins may be selected. An example of such a strong anionic exchange resin is that of the POROS HQ™ column. The resins for the columns listed above can be obtained from Amersham/Pharmacia (Piscataway, N.J.), PerSeptive Biosystems (Foster City, Calif.), TosoHaas (Montgomeryville, Pa.) and other suppliers.

The anion exchange material may be in the form of a monolith column or a traditional bead-based column. The ion exchange material can be in a column having a capacity of 0 to 0.5 mL column, 1 mL column, and more preferably, at least an 8 mL column, a 10 mL column, a 20 mL column, a 30 mL column, a 50 mL column, a 100 mL column, a 200 mL column, a 300 mL column, a 400 mL column, a 500 mL column, a 600 mL column, a 700 mL column, an 800 mL column, a 900 mL column, a 1000 mL (1 L) column, a 2000 mL (2 L) column, a 10 L column, a 20 L column, a 30 L column, a 40 L column, a 50 L column, a 60 L column, a 70 L column, an 80 L column, a 90 L column, a 100 L column, a 140 L column, or a column with a capacity greater than 140 L as well as any other column with a capacity between the volumes listed above. Alternatively, another vessel type may be used to contain the anion exchange resin solid support.

As shown in the working examples, regulation of the loading and flow rate enhances separation of the empty and full capsids. In one embodiment, the sample loading flow rate is less than or equal to the elution flow rate. For example, the loading flow rate may be in the range of about 10 mL/min to about 40 mL/min, about 15 mL/min to about 30 mL/min, or about 20 mL/min to about 25 mL/min, about 10 mL/min, about 20 mL/min, or about 30 cm/hr to about 135 cm/hr, for a 8 mL monolith column. Suitable flow rates may be extrapolated for a non-monolith column.

The specification describes salt concentrations herein with reference to NaCl for convenience. However, it will be understood that another salt of an equivalent ionic strength (e.g., KCl) may be substituted therefor, another salt having a different ionic strength, but its concentration adjusted to an equivalent ionic strength (e.g., $NH_4AC$), or a combination of salts, may be substituted. The formula for ionic strength is well known to those of skill in the art:

$$I = \frac{1}{2}\sum_{i=1}^{n} c_i z_i^2,$$

where $c_i$ is the molar concentration of ion i (M, mol/L), is the charge number of that ion, and the sum is taken over all ions in the solution. For a 1:1 electrolyte such as sodium chloride (NaCl), potassium chloride (KCl), formate ($HCO_2^-$), or acetate ($CH_2CO_2^-$) (e.g., $NH_4Ac$ or NaAc), the ionic strength is equal to the concentration. However, for a sulfate ($SO_4^{2-}$), the ionic strength is four times higher. Thus, where reference is made to a specific concentration of NaCl, or a range of concentrations, one of skill in the art can substitute another salt, or a mixture of suitable salts, adjusted to the appropriate concentration to provide an ionic strength equivalent to that provided for NaCl. As used herein this this may be termed a "salt equivalent", e.g., "NaCl or equivalent". This will be understood to include both a single salt, a mixture of NaCl with other salts, or a mixture of salts which do not include NaCl, but which are compatible with the apparatus and processes (e.g., affinity and/or anion exchange resin processes) described herein.

The novel FPLC strategy provided herein utilizes a strong anion exchange resin complex as described herein. The anion exchange resin binds the rAAV8 empty and full capsids are bound by a charge interaction while in buffer A (the running buffer). In one embodiment, the anion exchange resin column in equilibrated using Buffer A which contains about 200 nM NaCl to about 700 nM NaCl, or about 400 mM NaCl to about 650 mM NaCl, or salt equivalent. Suitable buffers may include ions contributed from a variety of sources, such as, e.g., N-methylpiperazine; piperazine; Bis-Tris; Bis-Tris propane; MES, Hepes, BTP or a phosphate buffer N-methyldiethanolamine; 1,3-diaminopropane; ethanolamine; acetic acid and the like. Such buffers are generally used at a neutral pH (e.g., about 6.5 to about 8, preferably, about 7 to about 7.5, or about 7.5). In one embodiment, a Tris buffer component is selected. In one embodiment, Buffer A contains about 20 mM Tris-Cl, about 400 nM NaCl or equivalent, pH 7.5.

The rAAV particles and intermediates become dissociated and returns to solution (suspension) in buffer B (the elution buffer). Buffer B is used to equilibrate the anion exchange resin. As provided herein, Buffer B is preferably at a pH of 10.2. While less optimal, the pH may be adjusted as low as about 10.0 or as high as about 10.4. In one embodiment, the buffer contains about 20 mM Bis-Tris Propane (BTP) and about 10 mM NaCl to about 40 nM NaCl (or salt equivalent).

A mixture containing rAAV8 empty and full particles may be suspended in about 100% Buffer A and applied to the column (vessel). The rAAV8 particles and intermediates bind to the resin while other components are carried out in the buffer. In one embodiment, the total flow rate of the buffer is kept constant; however, the proportion of Buffer B (the "elution" buffer) is gradually increased from 0% to 100% according to a programmed change in concentration (the "gradient").

In one embodiment, at least one nuclease digestion step is performed prior to loading the mixture onto the anion exchange resin, i.e., during the harvest of the rAAV particles and intermediates from the production cell culture. In a further embodiment, a second nuclease digestion step (e.g., Benzonase) is performed prior to loading the mixture onto the anion exchange resin. Suitably, this may be performed during affinity capture. For example, an additional wash step may be incorporated into the affinity method in which the selected nuclease(s) are pre-mixed with a buffer and used in a wash step. Suitably, the buffer is at neutral pH and a relatively low salt concentration, e.g., about 10 to about 100 mM, about 20 mM to about 80 mM, about 30 mM NaCl to about 50 mL, or about 40 mM, based on the ionic strength of NaCl or a salt equivalent to any of the preceding ranges or amounts. In one embodiment, the flow rate for this wash step is performed at a slower rate than the other wash steps to allow for greater exposure of the nuclease to the loaded rAAV particles and intermediates.

In one embodiment, the salt gradient has an ionic strength equivalent to at least about 10 mM NaCl to about 200 mM NaCl or salt equivalent. In another embodiment the salt gradient has an ionic strength equivalent to at least about 40 mM to about 190 mM NaCl, or about 70 nM to about 170 nM NaCl. In one embodiment, the AAV8 intermediates are separated from the anion exchange resin when the salt gradient reaches an ionic strength equivalent to about 50 nM NaCl or greater, or about 70 nM NaCl or greater.

At different points during this process, as described herein, the bound rAAV8 particles and rAAV8 empty intermediates dissociate and appear in the effluent. The effluent passes through two detectors which measure salt concentration (by conductivity) and protein concentration (by absorption of ultraviolet light at a predetermined wavelength). However, other suitable detection means may be used. As each protein is eluted it appears in the effluent as a "peak" in protein concentration and can be collected for further use.

As described herein, the fractions under the 260 nm elution peak containing the rAAV8 viral particles ("full") are collected and processed for further use. In one embodiment, the resulting rAAV8 preparation or stock contains a ratio of particles to vector genomes of 1. Optionally, the rAAV8 viral particles are placed in a suspension having a pH closer to a neutral pH which will be used for long-term storage and/or delivery to patients. Such a pH may be in the range of about 6.5 to about 8, or about 7 to about 7.5.

In one embodiment, particles elute in a pH of about 10.2 and the rAAV particles are at least about 50% to about 90% purified from AAV8 intermediates, or a pH of 10.2 and about 90% to about 99% purified from AAV8 intermediates. A stock or preparation of rAAV8 particles (packaged genomes) is "substantially free" of AAV empty capsids (and other intermediates) when the rAAV8 particles in the stock are at least about 75% to about 100%, at least about 80%, at least about 85%, at least about 90%, at least about 95%, or at least 99% of the rAAV8 in the stock and "empty capsids" are less than about 1%, less than about 5%, less than about 10%, less than about 15% of the rAAV8 in the stock or preparation.

In a further embodiment, the average yield of rAAV particles from loaded material is at least about 70%. This may be calculated by determining titer (genome copies) in the mixture loaded onto the column and the amount presence in the final elutions. Further, these may be determined based on q-PCR analysis and/or SDS-PAGE techniques such as those described herein (see figure legends) or those which have been described in the art.

For example, to calculate empty and full particle content, VP3 band volumes for a selected sample (e.g., in examples herein an iodixanol gradient-purified preparation where # of GC=# of particles) are plotted against GC particles loaded. The resulting linear equation (y=mx+c) is used to calculate the number of particles in the band volumes of the test article peaks. The number of particles (pt) per 20 μL loaded is then multiplied by 50 to give particles (pt)/mL. Pt/mL divided by GC/mL gives the ratio of particles to genome copies (pt/GC). Pt/mL-GC/mL gives empty pt/mL. Empty pt/mL divided by pt/mL and x 100 gives the percentage of empty particles.

Generally, methods for assaying for empty capsids and AAV vector particles with packaged genomes have been known in the art. See, e.g., Grimm et al., *Gene Therapy* (1999) 6: 1322-1330; Sommer et al., *Molec. Ther.* (2003) 7:122-128. To test for denatured capsid, the methods include subjecting the treated AAV stock to SDS-polyacrylamide gel electrophoresis, consisting of any gel capable of separating the three capsid proteins, for example, a gradient gel containing 3-8% Tris-acetate in the buffer, then running the gel until sample material is separated, and blotting the gel onto nylon or nitrocellulose membranes, preferably nylon. Anti-AAV capsid antibodies are then used as the primary antibodies that bind to denatured capsid proteins, preferably an anti-AAV capsid monoclonal antibody, most preferably the B1 anti-AAV-2 monoclonal antibody (Wobus et al, *J. Virol.* (2000) 74:9281-9293). A secondary antibody is then used, one that binds to the primary antibody and contains a means for detecting binding with the primary antibody, more preferably an anti-IgG antibody containing a detection molecule covalently bound to it, most preferably a sheep anti-mouse IgG antibody covalently linked to horseradish peroxidase. A method for detecting binding is used to semi-quantitatively determine binding between the primary and secondary antibodies, preferably a detection method capable of detecting radioactive isotope emissions, electromagnetic radiation, or colorimetric changes, most preferably a chemiluminescence detection kit. For example, for SDS-PAGE, samples from column fractions can be taken and heated in SDS-PAGE loading buffer containing reducing agent (e.g., DTT), and capsid proteins were resolved on pre-cast gradient polyacylamide gels (e.g., Novex). Silver staining may be performed using SilverXpress (Invitrogen, CA) according to the manufacturer's instructions. In one embodiment, the concentration of AAV vector genomes (vg) in column fractions can be measured by quantitative real time PCR (Q-PCR), Samples are diluted and digested with DNase I (or another suitable nuclease) to remove exogenous DNA. After inactivation of the nuclease, the samples are further diluted and amplified using primers and a TaqMan™ fluorogenic probe specific for the DNA sequence between the primers. The number of cycles required to reach a defined level of fluorescence (threshold cycle, Ct) is measured for each sample on an Applied Biosystems Prsim 7700 Sequence Detection System, Plasmid DNA containing identical sequences to that contained in the AAV vector is employed to generate a standard curve in the Q-PCR reaction. The cycle threshold (Ct) values obtained from the samples are used to determine vector genome titer by normalizing it to the Ct value of the plasmid standard curve. End-point assays based on the digital PCR can also be used.

In one aspect, an optimized q-PCR method is provided herein which utilizes a broad spectrum serine protease, e.g., proteinase K (such as is commercially available from Qiagen), More particularly, the optimized qPCR genome titer assay is similar to a standard assay, except that after the DNase 1 digestion, samples are diluted with proteinase K buffer and treated with proteinase K followed by heat inactivation. Suitably samples are diluted with proteinase K buffer in an amount equal to the sample size. The proteinase K buffer may be concentrated to 2 fold or higher.

Typically, proteinase K treatment is about 0.2 mg/mL, but may be varied from 0.1 mg/mL to about 1 mg/mL. The treatment step is generally conducted at about 55° C. for about 15 minutes, but may be performed at a lower temperature (e.g., about 37° C. to about 50° C.) over a longer time period (e.g., about 20 minutes to about 30 minutes), or a higher temperature (e.g., up to about 60° C.) for a shorter time period (e.g., about 5 to 10 minutes). Similarly, heat inactivation is generally at about 95° C. for about 15 minutes, but the temperature may be lowered (e.g., about 70 to about 90° C.) and the time extended (e.g., about 20 minutes to about 30 minutes). Samples are then diluted (e.g., 1000 fold) and subjected to TaqMan analysis as described in the standard assay.

Additionally, or alternatively, droplet digital PCR (ddPCR) may be used. For example, methods for determining single-stranded and self-complementary AAV vector genome titers by ddPCR have been described. See, e.g., M. Lock et al, Hu Gene Therapy Methods, Hum Gene Ther Methods. 2014 April; 25(2):115-25. doi: 10.1089/hgtb.201.3.131. Epub 2014 Feb. 14.

In one embodiment, the mixture which is applied to the anion exchange resin has been purified from contamination with materials present from the production system. Suitably, the mixture comprising the recombinant AAV8 viral particles and AAV8 intermediates contains less than about 10% contamination from non-AAV viral and cellular proteinaceous and nucleic acid materials, or less than about 5% contaminants, or less than 1% contaminating viral and cellular proteinaceous and nucleic acid materials. Thus, the mixture loaded onto the anion exchange resin is about 95% to about 99% free of contaminants.

As used herein, the term "contaminants" refer to host cell, viral, and other proteinaceous materials which are present in the production culture or are by-products thereof. This term does not include rAAV particles or rAAV intermediates having formed AAV capsids.

In one embodiment, a two-step chromatography method is provided in which affinity capture is utilized to separate a mixture of recombinant AAV8 viral particles and AAV8 capsid intermediates from production system contaminants. Advantageously, this processing has been found to allow approximately 3 times to 5 times the amount of starting material (based on the concentration of rAAV genome copies) to be processed using approximately 5 to 10 less resin, as compared to certain prior art approaches (e.g., one prior art approach utilized affinity capture after anion exchange and another utilized multiple, sequential, ion exchange resin columns).

This affinity capture is suitably performed using an antibody-capture affinity resin. In one embodiment, the solid support is a cross-linked poly(styrene-divinylbenzene) having an average particle size of about 50 μm and having an AAV-specific antibody. An example of one such commercially available affinity resin is POROS™ high performance affinity resin commercially available from Thermo Fischer Scientific. The resin contains ligands created by a proprietary technology based on camelid-derived single-domain antibody fragments coupled to the resin via carbonyldiimidazole (CDI). The ligand is a 13-kDa single-domain fragment that comprises the 3 CDRs that form the antigen binding domain and is efficiently produced by the yeast *Saccharomyces cerevisiae* in a production process free of animal components. Other suitable affinity resins may be selected or designed which contain an AAV-specific antibody, AAV8 specific antibody, or other immunoglobulin construct which is an AAV-specific ligand. Such solid supports may be any suitable polymeric matrix material, e.g., agarose, sepharose, sephadex, amongst others.

Suitable loading amounts may be in the range of about 2 to about $5\times10^{12}$ GC/mL resin, or less. Equivalent amounts may be calculated for other sized columns or other vessels. At this point prior to anion exchange resin separation as described herein, the term "genome copy" refers to the full particles in a mixture of both rAAV8 full particles and rAAV8 empties/intermediates.

In one embodiment, the mixture is buffer exchanged with the column equilibration/loading buffer. The method described herein utilizes a relatively high salt concentration for loading the column. In one embodiment, the mixture containing the AAV8 viral particles and AAV8 intermediates is loaded onto the affinity resin in a buffer having a high salt concentrations, e.g., about 400 nM NaCl to about 650 mM NaCl or another salt(s) having an equivalent ionic strength. The wash step for the affinity resin is thereafter performed at an even higher salt concentration, e.g., in the range of about 750 mM to about 1 M NaCl or equivalent. In one embodiment, the AAV8 mixture is maintained at a salt concentration of about 400 mM NaCl to about 650 mM NaCl, or equivalent prior to being applied to the anion exchange resin column. In a further embodiment, the rAAV8 mixture is maintained at this salt concentration following concentration and prior to loading onto the affinity resin. One example of a suitable buffer is Buffer A, containing about 200 nM to about 600 nM NaCl, or about 400 nM NaCl, or the ionically equivalent of another salt, about 10 mM to about 40 mM Tris-Cl or another buffer, at a neutral pH. The flow rate at loading may be a manufacturer's recommended value, e.g., about 149 cm/hr. A wash step using Buffer C is applied (1 M NaCl or an equivalent salt, 20 mM sodium citrate, neutral pH), followed by a wash with Buffer A, and use of Buffer B for elution. In one embodiment, Buffer B is about 200 nM to about 600 nM NaCl, or about 400 nM NaCl, or the ionically equivalent of another salt, about 10 mM to about 40 mM Tris-Cl, or about 20 nM Tris-Cl or another buffer. In one embodiment, this step is performed at the range recommended by the manufacturer, e.g., a low pH such as, e.g., about 2.5. In one embodiment, about 2 to about 8, or about 5 column volumes of buffer are used for these steps.

In one embodiment, at least one nuclease digestion step is performed prior to loading the mixture onto the anion exchange resin, i.e., during the harvest of the rAAV particles and intermediates from the production cell culture. In a further embodiment, a second nuclease digestion step is performed during affinity capture. For example, an additional wash step may be incorporated into the affinity method in which the selected nuclease(s) are pre-mixed with a buffer and used in a wash step. Suitably, the buffer is at neutral pH and a relatively low salt concentration, e.g., about 20 to about 60 mM, about 30 mM NaCl to about 50 mL, or about 40 mM, based on the ionic strength of NaCl or a salt equivalent to any of the preceding ranges or amounts. In one embodiment, the flow rate for this wash step is performed at a slower rate than the other wash steps to allow for greater exposure of the nuclease to the loaded rAAV particles and intermediates.

A single nuclease, or a mixture of nucleases, may be used in this step. Such nucleases may target single stranded DNA, double-stranded DNA, or RNA. While the examples illustrate use of a deoxyribonuclease (DNase) (e.g., Benzonase or Turbonuclease), other suitable nucleases are known, many of which are commercially available. Thus, a suitable nuclease or a combination of nucleases, may be selected. Further, the nuclease(s) selected for this step may be the same or different from the nuclease(s) used during the processing preceding the affinity step and which more immediately follows harvest from the cell culture.

In one embodiment, the load for the first affinity chromatography step is obtained following harvest and subsequent processing of cell lysates and/or supernatant of a production cell culture. This processing may involve at least one of the following processes, including, optional lysis, optional collection from supernatant (media), filtrations, clarification, concentration, and buffer exchange.

Numerous methods are known in the art for production of rAAV vectors, including transfection, stable cell line production, and infectious hybrid virus production systems which include Adenovirus-AAV hybrids, herpesvirus-AAV hybrids and baculovirus-AAV hybrids. See, e.g., G Ye, et al, Hu Gene Ther Clin Dev, 25: 212-217 (December 2014); R M Kotin, Hu Mol Genet, 2011, Vol. 20, Rev Issue 1, R2-R6; M. Mietzsch, et al, Hum Gene Therapy, 25: 212-222 (March 2014); T Virag et al, Hu Gene Therapy, 20: 807-817 (August 2009); N. Clement et al, Hum Gene Therapy, 20: 796-806 (August 2009); DL Thomas et al, Hum Gene Ther, 20: 861-870 (August 2009). rAAV production cultures for the production of rAAV virus particles may require; 1) suitable host cells, including, for example, human-derived cell lines such as HeLa, A549, or 293 cells, or insect-derived cell lines such as SF-9, in the case of baculovirus production systems; 2) suitable helper virus function, provided by wild type or mutant adenovirus (such as temperature sensitive adenovirus), herpes virus, baculovirus, or a nucleic acid construct providing helper functions in trans or in cis; 3) functional AAV rep genes, functional cap genes and gene products; 4) a transgene (such as a therapeutic transgene) flanked by AAV ITR sequences; and 5) suitable media and media components to support rAAV production.

A variety of suitable cells and cell lines have been described for use in production of AAV. The cell itself may be selected from any biological organism, including prokaryotic (e.g., bacterial) cells, and eukaryotic cells, including, insect cells, yeast cells and mammalian cells. Particularly desirable host cells are selected from among any mammalian species, including, without limitation, cells such as A549, WEHI, 3T3, 10T½, BHK, MDCK, COS 1, COS 7, BSC 1, BSC 40, BMT 10, VERO, WI38, HeLa, a HEK 293 cell (which express functional adenoviral E1), Saos, C2C12, L cells, HT1080, HepG2 and primary fibroblast, hepatocyte and myoblast cells derived from mammals including human, monkey, mouse, rat, rabbit, and hamster. The selection of the mammalian species providing the cells is not a limitation of this invention; nor is the type of mammalian cell, i.e., fibroblast, hepatocyte, tumor cell, etc.

AAV sequences may be obtained from a variety of sources. For example, a suitable AAV sequence may be obtained as described in WO 2005/033321 or from known sources, e.g., the American Type Culture Collection, or a variety of academic vector core facilities. Alternatively, suitable sequences are synthetically generated using known techniques with reference to published sequences. Examples of suitable AAV sequences are provided herein.

In addition to the expression cassette, the cell contains the sequences which drive expression of an AAV capsid in the cell (cap sequences) and rep sequences of the same source as the source of the AAV ITRs found in the expression cassette, or a cross-complementing source. The AAV cap and rep sequences may be independently selected from different AAV parental sequences and be introduced into the host cell in a suitable manner known to one in the art. While the full-length rep gene may be utilized, it has been found that smaller fragments thereof, i.e., the rep78/68 and the rep52/40 are sufficient to permit replication and packaging of the AAV.

In one embodiment, the host cell contains at least the minimum adenovirus DNA sequences necessary to express an E1a gene product, an E1b gene product, an E2a gene product, and/or an E4 ORF6 gene product. In embodiments in which the host cell carries only E1, the E2a gene product and/or E4 ORF6 gene product may be introduced via helper plasmid or by adenovirus co-infection. In another embodiment, the E2a gene product and/or E4 ORF6 may be substituted by herpesvirus helper functions. The host cell may contain other adenoviral genes such as VAI RNA, but these genes are not required. In one embodiment, the cell used does not carry any adenovirus gene other than E1, E2a and/or E4 ORF6; does not contain any other virus gene which could result in homologous recombination of a contaminating virus during the production of rAAV; and it is capable of infection or transfection by DNA and expresses the transfected gene (s).

One cell type useful in the methods and systems described herein is a host cell stably transformed with the sequences encoding rep and cap, and which is transfected with the adenovirus E1, E2a, and E4 ORF6 DNA and a construct carrying the expression cassette as described above. Stable rep and/or cap expressing cell lines, such as B-50 (International Patent Application Publication No. WO 99/15685), or those described in U.S. Pat. No. 5,658,785, may also be similarly employed. Another desirable host cell contains the minimum adenoviral DNA which is sufficient to express E4 ORF6. Yet other cell lines can be constructed using the novel modified cap sequences.

The preparation of a host cell involves techniques such as assembly of selected DNA sequences. This assembly may be accomplished utilizing conventional techniques. Such techniques include cDNA and genomic cloning, which are well known and are described in Sambrook et al., Molecular Cloning: A Laboratory Manual, Cold Spring Harbor Press, Cold Spring Harbor, N.Y., including polymerase chain reaction, synthetic methods, and any other suitable methods which provide the desired nucleotide sequence.

The required components for AAV production (e.g., adenovirus E1a, E1b, E2a, and/or E4 ORF6 gene products, rep or a fragment(s) thereof, cap, the expression cassette, as well as any other desired helper functions), may be delivered to the packaging host cell separately, or in combination, in the form of any genetic element which transfer the sequences carried thereon.

Alternatively, one or more of the components required to be cultured in the host cell to package an expression cassette in an AAV capsid may be provided to the host cell in trans using a suitable genetic element.

Suitable media known in the art may be used for the production of rAAV vectors. These media include, without limitation, media produced by Hyclone Laboratories and JRH including Modified Eagle Medium (MEM), Dulbecco's Modified Eagle Medium (DMEM), custom formulations such as those described in U.S. Pat. No. 6,566,118, and Sf-900 II SFM media as described in U.S. Pat. No. 6,723, 551, each of which is incorporated herein by reference in its entirety, particularly with respect to custom media formulations for use in production of recombinant AAV vectors.

rAAV production culture media may be supplemented with serum or serum-derived recombinant proteins at a level of 0.5%-20% (v/v or w/v). Alternatively, as is known in the art, rAAV vectors may be produced in serum-free conditions which may also be referred to as media with no animal-derived products. One of ordinary skill in the art may appreciate that commercial or custom media designed to support production of rAAV vectors may also be supplemented with one or more cell culture components know in the art, including without limitation glucose, vitamins, amino acids, and or growth factors, in order to increase the titer of rAAV in production cultures.

rAAV production cultures can be grown under a variety of conditions (over a wide temperature range, for varying lengths of time, and the like) suitable to the particular host cell being utilized. As is known in the art, rAAV production cultures include attachment-dependent cultures which can be cultured in suitable attachment-dependent vessels such as, for example, roller bottles, hollow fiber filters, microcarriers, and packed-bed or fluidized-bed bioreactors. rAAV vector production cultures may also include suspension-adapted host cells such as HeLa, 293, and SF-9 cells which can be cultured in a variety of ways including, for example, spinner flasks, stirred tank bioreactors, and disposable systems such as the Wave bag system.

rAAV vector particles may be harvested from rAAV production cultures by lysis of the host cells of the production culture or by harvest of the spent media from the production culture, provided the cells are cultured under conditions known in the art to cause release of rAAV particles into the media from intact cells, as described more fully in U.S. Pat. No. 6,566,118). Suitable methods of lysing cells are also known in the art and include for example multiple freeze/thaw cycles, sonication, microfluidization, and treatment with chemicals, such as detergents and/or proteases.

At harvest, rAAV production cultures may contain one or more of the following: (1) host cell proteins; (2) host cell DNA; (3) plasmid DNA; (4) helper virus; (5) helper virus proteins; (6) helper virus DNA; and (7) media components including, for example, serum proteins, amino acids, transferrins and other low molecular weight proteins.

In some embodiments, the rAAV production culture harvest is clarified to remove host cell debris. In some embodiments, the production culture harvest is clarified by filtration through a series of depth filters including, for example, a grade DOHC Millipore Millistak+HC Pod Filter, a grade A1HC Millipore Millistak+HC Pod Filter, and a 0.2 µm Filter Opticap XL10 Millipore Express SHC Hydrophilic Membrane filter. Clarification can also be achieved by a variety of other standard techniques known in the art, such as, centrifugation or filtration through any cellulose acetate filter of 0.2 µm or greater pore size known in the art. Still other suitable depth filters, e.g., in the range of about 0.045 µm to about 0.2 µm or other filtration techniques may be used.

Suitably, the rAAV production culture harvest is treated with a nuclease, or a combination of nucleases, to digest any contaminating high molecular weight nucleic acid present in the production culture. The examples herein illustrate a DNAse, e.g., Benzonase® digestion performed under standard conditions known in the art. For example, a final concentration of 1 unit/mL to 2.5 units/mL of Benzonase® is used at a temperature ranging from ambient temperature to 37° C. for a period of 30 minutes to several hours, or about 2 hours. In another example, a turbonuclease is used. However, one of skill in the art may utilize other another suitable nuclease, or a mixture of nucleases. Examples of other suitable nuclease is described earlier in this specification.

The mixture containing full rAAV particles and rAAV intermediates (including empty capsids) may be isolated or purified using one or more of the following purification steps: tangential flow filtration (TFF) for concentrating the rAAV particles, heat inactivation of helper virus, rAAV capture by hydrophobic interaction chromatography, buffer exchange by size exclusion chromatography (SEC), and/or nanofiltration. These steps may be used alone, in various combinations, or in different orders. In some embodiments, the method comprises all the steps in the order as described below.

In some embodiments, the Benzonase®-treated mixture is concentrated via tangential flow filtration ("TFF"). Large scale concentration of viruses using TFF ultrafiltration has been described by R. Paul et al., Hu Gene Therapy, 4:609-615 (1993). TFF concentration of the feedstream enables a technically manageable volume of feedstream to be subjected to the chromatography steps of the present method and allows for more reasonable sizing of columns without the need for lengthy recirculation times. In some embodiments, the rAAV feedstream is concentrated between at least two-fold and at least ten-fold. In some embodiments, the feedstream is concentrated between at least ten-fold and at least twenty-fold. In some embodiments, the feedstream is concentrated between at least twenty-fold and at least fifty-fold. One of ordinary skill in the art will also recognize that TFF can also be used at any step in the purification process where it is desirable to exchange buffers before performing the next step in the purification process.

As used herein, the singular form of the articles "a," "an," and "the" includes plural references unless indicated otherwise. For example, the phrase "a virus particle" includes one or more virus particles.

As used herein, the terms "comprise", "comprising", "contain", "containing", and their variants are open claim language, i.e., are permissive of additional elements. In contrast, the terms "consists", "consisting", and its variants are closed claim language, i.e., exclusive additional elements.

Reference to "about" a value or parameter herein includes (and describes) embodiments that are directed to that value or parameter per se. For example, description referring to "about X" includes description of "X." In the context of pH values, "about" refers to a variability of ±0.2 from the given value. For example, "about 10.2" encompasses to 10.0 to 10.4. As to other values, unless otherwise specified "about" refers to a variability of ±10% from a given value. In certain embodiments, the variability may be 1%, 5%, 10%, or values therebetween.

While the purification methods described herein are designed particularly for separating full rAAV8 particles from empty rAAV8 intermediates, one of skill in the art may apply these techniques to other rAAV which are closely related to AAV8. and in particularly AAV having about 99% identity over the full-length VP1, VP2 or VP3 protein of the AAV8 capsid as defined herein, and/or 100% identity over the AAV8 capsid antibody binding region for the affinity resin.

In still another aspect, a scalable method for separating full AAV8 viral particles from AAV8 intermediates by using an anti-AAV antibody based affinity capture resin followed by an anion exchange resin is provided. In one embodiment, the mixture containing the AAV8 viral particles and AAV8 intermediates is loaded onto the affinity resin in a buffer having a high salt concentrations, e.g., about 400 nM NaCl to about 650 mM NaCl or another salt(s) having an equivalent ionic strength. The wash step for the affinity resin is thereafter performed at an even higher salt concentration, e.g., in the range of about 750 mM to about 1 M NaCl or equivalent. In one embodiment, the AAV8 mixture is maintained at a salt concentration of about 400 mM NaCl to about 650 mM NaCl, or equivalent prior to being applied to the anion exchange resin column. In one embodiment, the affinity capture includes a nuclease digestion step. In a further embodiment, the rAAV8 mixture is maintained at this salt concentration following concentration and prior to loading onto the affinity resin.

In a further embodiment, the affinity purified mixture containing the viral particles having packaged genomic sequences are separated from genome-deficient AAV8 capsid intermediates by subjecting the mixture to fast performance liquid chromatography at a pH of about 10.2. More particularly, the AAV8 viral particles and AAV8 intermediates are bound to an anion exchange resin equilibrated at a pH of about 10.2, and subjected to a salt gradient while monitoring eluate for ultraviolet absorbance at about 260 and about 280, wherein the AAV8 full capsids are collected from a fraction which is eluted when the ratio of A260/A280 reaches an inflection point.

In one aspect, a method for separating AAV8 viral particles from AAV8 capsid intermediates is provided which involves:
(a) mixing a suspension comprising recombinant AAV8 viral particles and AAV8 capsid intermediates and a Buffer A comprising 20 mM to 50 mM Bis-Tris propane (BTP) and a pH of about 10.2;
(b) loading the suspension of (a) onto a strong anion exchange resin column;
(c) washing the loaded anion exchange resin with Buffer 1% B which comprises a salt having the ionic strength of 10 mM to 40 mM NaCl and BTP with a pH of about 10.2;
(d) applying an increasing salt concentration gradient to the loaded and washed anion exchange resin, wherein the salt gradient is the equivalent of about about 10 mM to about 400 mM NaCl, or about 10 mM to about 200 mM, or about 10 mM to about 190 mM; and
(e) collecting rAAV8 particles from elute obtained at a salt concentration equivalent to at least 70 mM NaCl, where the rAAV8 particles are at least about 90% purified from AAV8 intermediates.

In one embodiment, the intermediates are eluted from the anion exchange resin when the salt concentration is the equivalent of greater than about 50 mM NaCl. In still a further embodiment, Buffer A is further admixed with NaCl to a final concentration of 1M in order to form or prepare Buffer B. In yet another embodiment, the salt gradient has an ionic strength equivalent to 10 mM to about 190 mM NaCl. In still a further embodiment, the salt gradient has an ionic strength equivalent to 20 mM to about 190 mM NaCl, or about 20 mM to about 170 mM NaCl. The elution gradient may be from 1% buffer B to about 19% Buffer B. Optionally, the vessel containing the anion exchange resin is a monolith column; loading, washing, and eluting occur in about 60 column volumes.

In still a further embodiment, a method for separating recombinant AAV8 viral particles containing DNA comprising genomic sequences from genome-deficient (empty) AAV8 capsid intermediates is provided. The method involves:
(a) forming a loading suspension comprising recombinant AAV8 viral particles and empty AAV8 capsid intermediates which have been purified to remove non-AAV materials from an AAV producer cell culture in which the particles and intermediates were generated; and a Buffer A comprising 20 mM Bis-Tris propane (BTP) and a pH of about 10.2;
(b) loading the suspension of (a) onto a strong anion exchange resin, said resin being in a vessel having an inlet for flow of a suspension and/or solution and an outlet permitting flow of eluate from the vessel;
(c) washing the loaded anion exchange resin with Buffer 1% B which comprises 10 mM NaCl and 20 mM BTP with a pH of about 10.2;
(d) applying an increasing salt concentration gradient to the loaded and washed anion exchange resin, wherein the salt gradient ranges from 10 mM to about 190 mM NaCl, inclusive of the endpoints, or an equivalent; and
(e) collecting the rAAV particles from eluate, said rAAV particles being purified away from 9 intermediates.

In one embodiment, the pH is 10.2 and the rAAV particles are at least about 90% purified from AAV8 intermediates. In a further embodiment, the average yield of rAAV particles is at least about 70%.

In a further embodiment, the rAAV8 producer cell culture is selected from a mammalian cell culture, a bacterial cell culture, and an insect cell culture, wherein said producer cells comprise at least (i) nucleic acid sequence encoding an AAV8 capsid operably linked to sequences which direct expression of the AAV8 capsid in the producer cells; (ii) a nucleic acid sequence comprising AAV inverted terminal repeat sequences and genomic transgene sequences for packaging into the AAV8 capsid; and (iii) functional AAV rep sequences operably linked to sequences which direct expression thereof in the producer cells. In another embodiment, producer cells further comprise helper virus sequences required for packaging and replication of the AAV8 into a viral particle.

In still another embodiment, the material harvested from the cell culture is applied to an affinity resin to separate contaminants from AAV8 viral particles and empty AAV8 capsid intermediates.

In a further embodiment, the affinity resin separation comprises:
(i) equilibrating the affinity resin with Buffer A1 which comprises about 200 mM to about 600 mM NaCl, about 20 mM Tris-Cl and a neutral pH prior to applying the material to the affinity resin;
(ii) washing the loaded resin of (a) with Buffer C1 which comprises about 800 mM NaCl to about 1200 mM NaCl, 20 mM Tris-Cl and a neutral pH; (iii) washing the Buffer C1-washed resin of (b) with Buffer A1 to reduce salt concentration;
(iv) washing the affinity resin of (c) with Buffer B which comprises about 200 nM to about 600 nM NaCl, 20 mM Sodium Citrate, pH about 2.4 to about 3; and
(v) collecting the eluate of (iv) which comprises the full AAV8 particles and the empty AAV8 capsid fraction for loading onto the anion exchange resin.

The following examples are illustrative of methods for producing AAV particles in the supernatant of cell cultures.

EXAMPLES

A two-step chromatography purification scheme is described which selectively captures and isolates the genome-containing AAV vector particles from the clarified, concentrated supernatant of HEK 293 cells five days post transfection. The load for the first chromatography step using an AAV8-specific affinity resin, may consist of filter-clarified, concentrated supernatant harvested from cell culture vessels are treated with a nuclease (e.g., Benzonase at 37° C. for 2 hours) followed by a hypertonic shock (e.g., 5 M NaCl for 2 h). Prior to loading, the bulk harvest is buffer-exchanged with the column equilibration/loading buffer (Buffer A) incubated overnight at 4° C., and then filtered with a suitable depth filter (e.g., 0.2 μm PES depth filter (Sartorius)). The sample is applied to a column according to the following method:

Equilibration: Buffer A (400 mM NaCl, 20 mM Tris-Cl, pH 7.5)
Wash 1: Buffer D (1.5 mM $MgCl_2$, 40 mM NaCl, 20 mM Tris-Cl, pH 7.5)
  Premix with 150 μl (37,500 u) Benzonase Nuclease
  Reduce the flow rate to 30 cm·$hr^{-1}$ (5 ml/min)
Wash 2: Buffer C (1M NaCl, 20 mM Tris-Cl, pH 7.5)
Wash 3: Buffer A Elution: Buffer B (400 mM NaCl, 20 mM Sodium Citrate, pH 2.5)

Re-equilibration: Poros-9 Buffer A

A volume of 500 µl of Neutralization Buffer (0.01% Pluronic F-68, 0.2 M Bis-Tris propane, pH10.2) is pre-added to the elution fraction tubes and upon completion of the run, the 5-ml fractions under the main 280-nm elution peak (typically three fractions) are pooled and diluted 50× with AEX Buffer A-10.2 (20 mM Bis-Tris Propane pH 10.2) plus Pluronic F-68 (0.001% final) in a polypropylene bottle.

Anion exchange chromatography is subsequently performed to separate the full or DNA-carrying viral particles from the contaminating empty particles in the second step. Specifically, the diluted column eluate from the capture step is applied to a pre-equilibrated CIMmultus QA-8 ml monolith column (BIA Separations) and the following method is run:

Flow rate: 10 ml/min

Equilibration: 20 CV AEX Buffer 1% B (20 mM Bis-Tris Propane pH 10.2, 10 mM NaCl)

Sample Application: approx. 800 ml for three diluted POROS 8 or 9 fractions

Wash 1: 10 CV AEX Buffer 1% B-10.2

Elution: 1-19% AEX Buffer B-10.2 (20 mM Bis-Tris Propane pH 10.2, 1 M NaCl)

Linear gradient in 60 CV @ 10-20 ml/min

Strip: 20 CV 100% AEX Buffer B-10.2

Re-equilibration: 10 CV AEX Buffer 1% B-10.2

A volume of 370 µl of AEX Neutralization Buffer (0.027% Pluronic F-68, 1M Bis-Tris pH 6.3) may be pre-added to the elution tubes to minimize exposure of the vector to the high pH after elution. Finally, the 10-ml fractions under the main 260-nm elution peak are ultimately pooled and concentrated/diafiltrated with a formulation buffer using a hollow fiber membrane.

Example 1: Separation of Full rAAV Particles from Empty AAV8 Capsids

AAV8 vector particles containing single stranded DNA genomes were produced by triple plasmid transfection in HEK293 cells (Lock et al. 2010, Hum Gene Ther, 21(1): 1259-1271) and the clarified production culture supernatant was purified by affinity chromatography on PorosAAV8™ resin (ThermoFisher). The clarified supernatant was loaded to the affinity column at neutral pH in 400 mM salt and eluted with a low pH (~2.5) buffer. The eluate was immediately adjusted to neutral pH and then diluted 50-fold into a Bis-Tris-propane (BTP) buffer A at pH10. $7 \times 10^{13}$ vector genome copies (GC) of the material was loaded onto a 0.1 mL CIMac-QA™ column (Bia Separations) at 2 mL/min. The column was washed in buffer A with 20 mM NaCl, eluted with a shallow (20-180 mM NaCl, 60 CV) salt gradient at the same flow-rate and then stripped with high salt Buffer B (20 mM BTP, 1M NaCl). A chromatogram of the CIMac-QA™ run is shown in FIG. 1. A major peak (P2) was observed in the elution gradient and notably the A260/A280 ratio of this peak was greater than one, as would be expected for a pure particle population containing vector genomes. A smaller peak (P1) was also observed in the gradient and in this case the peak absorbance at 280 nm is higher than at 260 nm. A third peak (P3) is observed as a trailing shoulder to P2 and also has an A260/A280 ratio of less than one. A low A260/280 peak ratio (<1) is indicative of empty AAV particles lacking a vector genome. Thus, the A260/280 absorbance ratios of the three peaks observed in the elution gradient suggest the existence of a full particle population and two distinct empty particle populations that can be partially resolved on strong anion exchange columns at pH 10 by application of a shallow elution gradient.

Figure 2A:
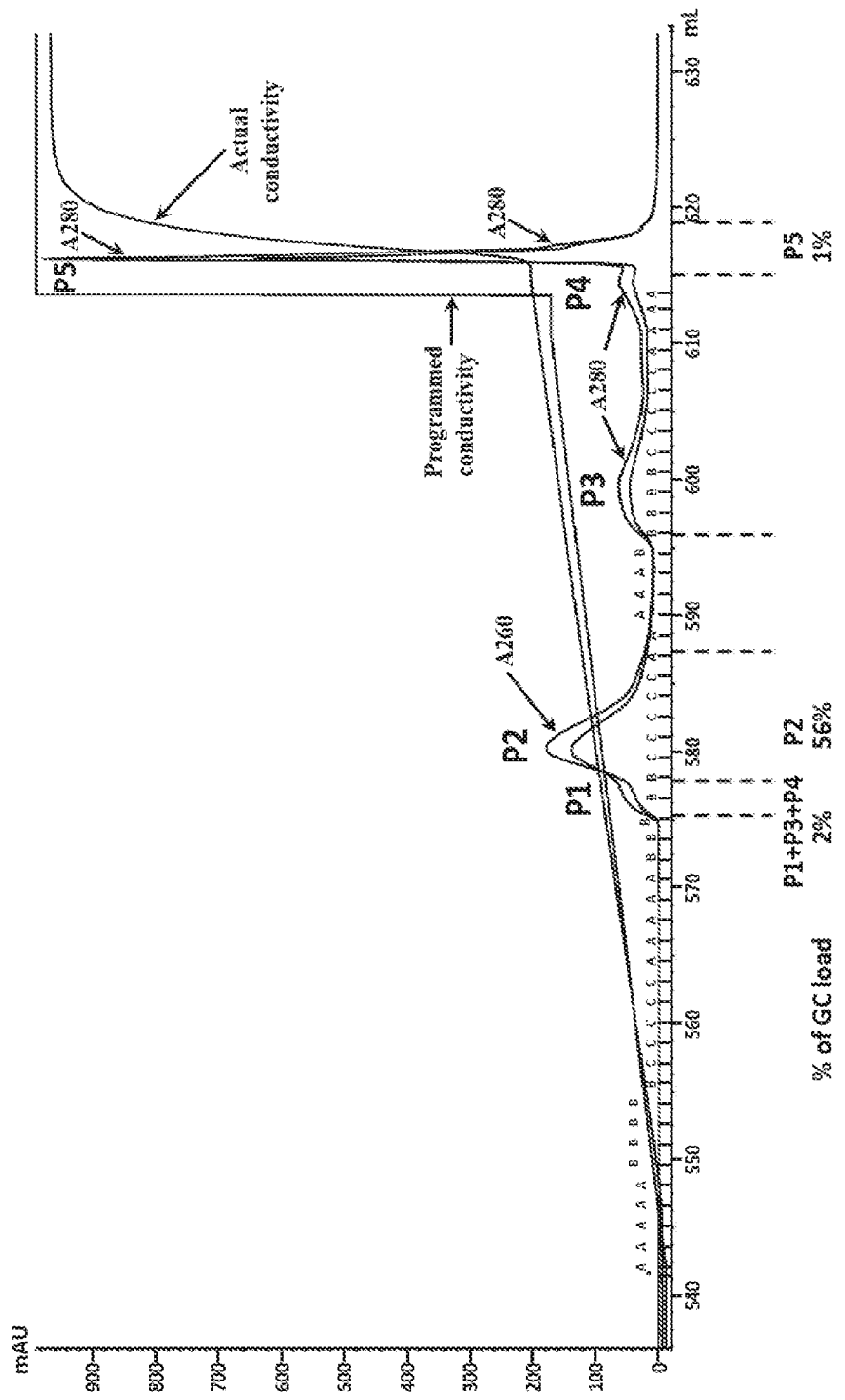

Example 2: Purification Method Purifies Full Particles from an Excess of Empty Particles A separate AAV8 vector was produced at larger scale by triple plasmid transfection of HEK293 cells (Lock et al. 2010, Hum Gene Ther, 21(1): 1259-1271). This vector contained a self-complementary AAV genome which is known to be packaged less efficiently than single stranded genomes. The clarified supernatant from the production culture was purified using a PorosAAV8™ affinity column (ThermoFisher) at neutral pH in 400 mM salt and eluted with a low pH (~2.5) buffer. The eluate was immediately adjusted to neutral pH and then diluted 50-fold into a Bis-Tris-propane (BTP) buffer A at pH 10.2. $3.8 \times 10^{13}$ vector genome copies (GC) of the affinity-purified vector material was loaded onto an 8 mL CIMmultus-QA column (Bia Separations) at 10 mL/min. The column was washed in buffer A with 20 mM NaCl, eluted with a shallow (10-190 mM NaCl, 60 CV) salt gradient at 20 mL/min and then stripped with high salt Buffer B (10 mM BTP, 1M NaCl). A chromatogram of this run is shown in FIG. 2A. Five major peaks (P1-P5) were observed and as in the previous smaller scale run (FIG. 1, Example 1) a major peak (P2) was noted in the elution gradient with an A260/A280 ratio greater than one. This peak contained the majority of the genome copies (GC) loaded to the column as measured by polymerase chain reaction (PCR) (FIG. 2A). The three other peaks in the elution gradient (P1, P3 and P4) collectively contained very few genome copies and had A260/A280 ratios greater than one, indicative of empty particles. In contrast to the observed peak separation at pH10 (FIG. 1), in the pH 10.2 run P1 is less well resolved from P2, whereas P3 is better separated. In addition, at pH 10.2, a newly observed major peak (P5) with an A260 ratio greater than one and containing very low amounts of vector genomes is apparent in the column strip fraction. Together these observations demonstrate that fine adjustments in pH can be employed to separate different particle populations. An SDS-PAGE-based method to quantify total capsids was developed and the peak fractions further analyzed (FIG. 2B). In this method, a reference preparation purified by iodixanol gradient purification and known to contain 100% full capsids is serially diluted and run on an SDS-PAGE gel alongside a similarly diluted test article. The stained gel is scanned and the area under the VP3 capsid protein peaks is determined. In the case of the full reference standard, the GC number loaded equates to vector particle number and hence a standard curve of particle number versus VP3 band volume can be obtained. The standard curve is used to determine the number of particles in the purified peak fractions. The number of empty particles can be obtained by subtracting GC from total particles and used to calculate the empty: full (E: F) ratio and the percentage of empty particles in a sample. It should be noted that the amount of the peak fractions loaded to the gel were adjusted such that particle numbers fall on the standard curve and therefore that particle numbers derived are not representative of relative amounts in the peaks. The results of this assay confirm that P1, P3, P4 and P5 are comprised of empty particle populations. The distinct charge properties of these populations resulting in different affinities to the anion exchange column, likely indicate the presence of disparate intermediates in particle packaging and assembly. P2 on the other hand is highly enriched for full particles. Overall, the data demonstrate that affinity purified vector contains both full and empty vector populations and that several empty "intermediates" (e.g. partially packaged, partially assembled capsids) are present.

These particle populations can be separated from one another by the anion exchange chromatography method employed. In addition, the large size of P5 in comparison to P2 supports the observation that self-complementary vectors are poorly packaged and demonstrates the ability of the purification method to purify full particles from an excess of empty particles.

Figure 3A:
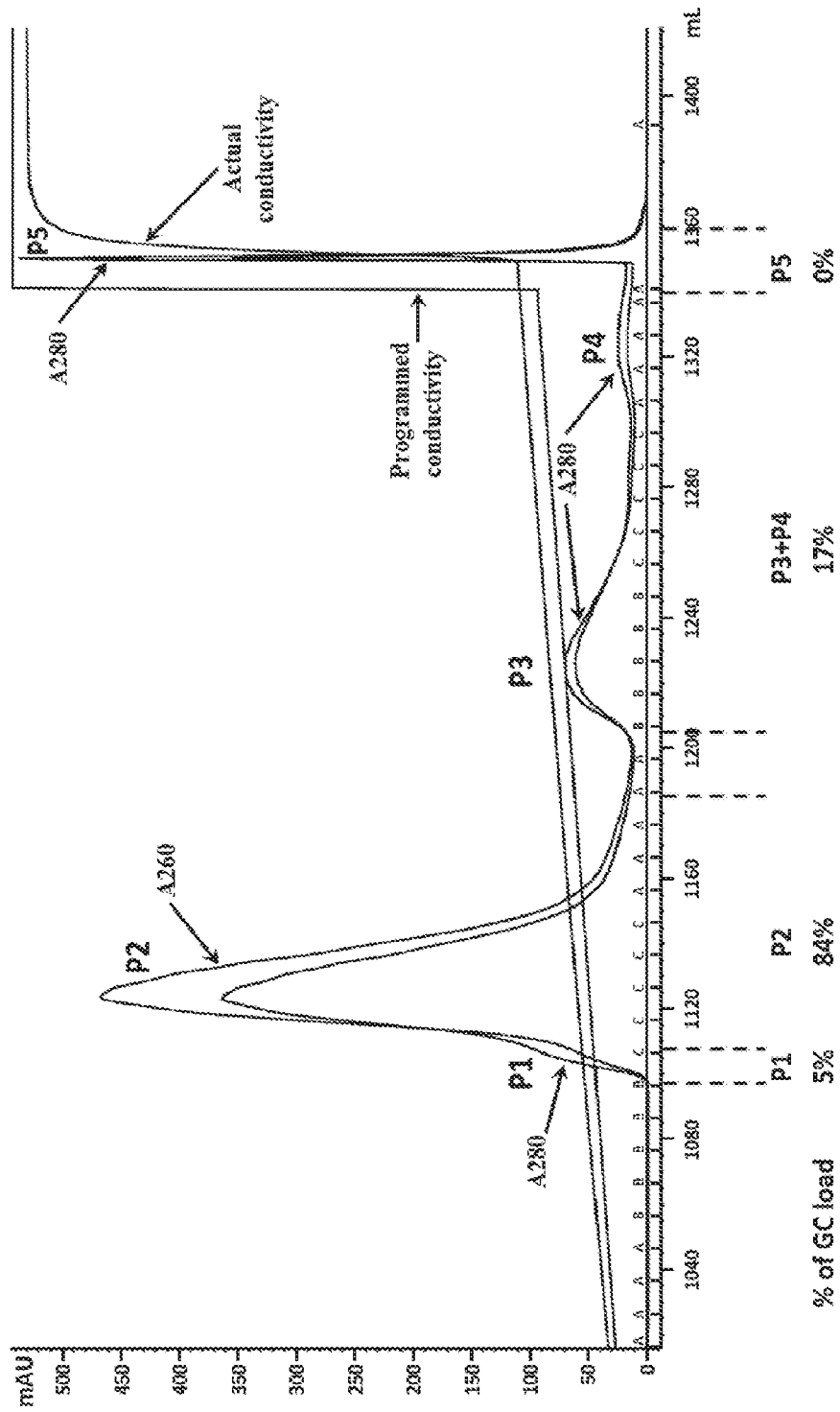

Example 3: Purification Method is Scalable and Maintains Robust Peak Separation with Scale A separate PorosAAV8™ affinity resin-purified AAV8 vector preparation (single stranded genome) containing 2.1× $10^{15}$ GC was loaded onto an 8 mL CIMmultus-QA column in Bis-Tris-propane (BTP) buffer A at pH10.2 and 10 mL/min. The column was washed in buffer A with 20 mM NaCl, eluted with a shallow (10-190 mM NaCl, 60 CV) salt gradient at 20 mL/min and then stripped with high salt Buffer B (20 mM BTP, 1M NaCl). Despite the increased amount of vector loaded, a similar chromatographic profile was obtained with 5 peaks (P1-P5) detected in the elution gradient and the column strip (FIG. 3a). Analysis of GC content once again showed that the majority of the full particles eluted in P2 (Data not shown). The SDS-PAGE-based particle quantification method described above (Example 2) was used to further analyze peak fractions. The results confirm the earlier conclusions (Example 2) that P1, P3, P4 and P5 are comprised of empty particle populations which likely represent intermediates in particle packaging and assembly. P2 on the other hand is highly enriched for full particles. P1 is not completely separated from P2 but as will be obvious to those with skill in the art, further enrichment of the full particle population and reduction of empty capsid content might be achieved by sub-fractionation of P2 and avoidance of those fractions at the front portion of the peak. Alternatively, the sample could be rerun at a lower pH where P1 and P2 are separated (Example 1). Overall, these results demonstrate the scalability of the purification method and the robustness of peak separation with scale.

Example 4: qPCR Genome Titer Assays

For the standard qPCR genome titer assay, purified vectors are diluted 10-fold with 1×DNase I reaction buffer and treated with DNase I (Roche Applied Science, Indianapolis, Ind.) at 400 U/mL for 30 minutes at 37° C. Treated samples are then diluted a further 1,000-fold in dilution buffer (1×PCR buffer; Applied Biosystems Inc., Foster City, Calif. plus 2 ng/µL sheared salmon sperm DNA; Invitrogen Corp., Carlsbad, Calif.). 5 µl are added to a 50 µl reaction along with Taqman Universal PCR master-mix (Applied Biosystems Inc.) and TaqMan primers and probes directed against various regions of the transgene cassette (Applied Biosystems Inc.; 0.304 and 0.2 µM final concentration respectively). The plasmid standard curves are prepared by restriction enzyme linearization and purification by the Qiaquick PCR purification kit (Qiagen Inc. Valencia Calif.). The linearized DNA was quantified by UV spectrophotometry and 10-fold serially diluted from $10^8$ to 10 copies per 5 µL. Diluted standard curves are assembled into 50 µl PCR reaction volumes as for the vector samples. The samples are PCR amplified with a SDS7500 real-time PCR instrument (Applied Biosystems Inc.) using a two-step cycling protocol (40 cycles: 95° C. for 15 seconds, 60° C. for 1 minute) preceded by a 10 minute incubation at 95° C.

The optimized qPCR (oqPCR) genome titer assay is performed in a manner similar to the standard assay, but additionally, after the DNase I digestion, samples were diluted with equal volume of 2× proteinase K buffer and treated with proteinase K (Qiagen Inc.; 0.2 mg/mL, 55° C., 30 minutes) followed by heat inactivation at 95° C. for 15 minutes. Samples were then diluted 1,000 folds and subjected to TaqMan analysis as described in standard assay. In addition, all dilutions were made in the presence of 0.1% Pluronic F68 (Invitrogen Corp.)

TABLE 1

AAV titers determined by standard or optimized qPCR methods.

| Vector Name | Titer by SD qPCR (GC/ml) | Titer by opt. qPCR (GC/ml) | Ratio |
| --- | --- | --- | --- |
| AAV2/8sc.CMV.EGFP.RBG | 9.61E+10 | 4.42E+11 | 4.60 |
| AAV2/8.CB7.CI.EGFP.RBG | 1.44E+13 | 3.25E+13 | 2.26 |
| AAV2/8.TBG.PI.Cre.RBG | 2.54E+13 | 8.35E+13 | 3.29 |
| AAV2/8.CMV.TurboRFP.RBG | 8.31E+12 | 2.12E+13 | 2.55 |
| AAV2/8.CMV.TurboRFP.RBG | 1.32E+13 | 2.53E+13 | 1.92 |
| AAV2/8.CMV.PI.Cre.RBG | 2.60E+13 | 4.99E+13 | 1.92 |
| AAV2/8.TBG.PI.Cre.RBG | 1.68E+13 | 5.47E+13 | 3.26 |
| AAV2/8.TBG.PI.ffluciferase.RBG | 3.60E+12 | 1.20E+13 | 3.33 |

Genome titers of 8 AAV lots were determined by standard or optimized qPCR assays targeting polyA sequence derived from rabbit β-globulin gene. The difference in titers obtained from these 2 methods is ranging from 2 to 5 fold.

Sequence Listing Free Text

The following information is provided for sequences containing free text under numeric identifier <223>.

| SEQ ID NO: (containing free text) | Free text under <223> |
| --- | --- |
| 1 | <223> Adeno-associated virus 8 vp1 capsid protein |

All publications and references to GenBank and other sequences cited in this specification, together with priority applications U.S. Provisional Patent Application No. 62/322,098, filed Apr. 13, 2016, and U.S. Provisional Patent Application No. 62/266,341, filed Dec. 11, 2015, are incorporated herein by reference. While the invention has been described with reference to particularly preferred embodiments, it will be appreciated that modifications can be made without departing from the spirit of the invention.

The invention claimed is:

1. A method for separating recombinant adeno-associated virus (AAV) 8 (rAAV8) viral particles having packaged genomic sequences from genome-deficient AAV8 capsid intermediates, said method comprising:
    (a) performing filtration through a series of depth filters to afford a clarified rAAV8 production culture harvest;
    (b) treating the clarified rAAV8 production culture harvest of (a) with a nuclease or a combination of nucleases to digest contaminating high molecular weight nucleic acid and to afford a mixture comprising rAAV8 viral particles and genome-deficient AAV8 capsid intermediates;
    (c) concentrating the nuclease-treated mixture of (b) via tangential flow filtration (TFF) to afford a concentrated rAAV8 feedstream;
    (d) contacting the concentrated rAAV8 feedstream of (c) comprising the rAAV8 viral particles and genome-deficient AAV8 capsid intermediates with a high-performance AAV8-capsid binding affinity resin to afford purified mixture;
    (e) performing anion exchange chromatography by anion exchange resin on the affinity purified mixture of (d) containing the rAAV8 viral particles at a pH of 10.0 to 10.4;
    (f) monitoring an eluate of (e) for ultraviolet absorbance at 260 nm (A260) and at 280 nm (A280); and
    (g) collecting rAAV8 viral particles from fractions eluted when the ratio of A260 to A280 (A260/A280) reaches an inflection point.

2. The method according to claim 1, wherein the inflection point is when the curve ratio of A260/A280 changes from less than 1 to greater than 1.

3. The method according to claim 1, wherein the anion exchange chromatography of (e) is performed at a salt gradient which has an ionic strength equivalent to at least about 20 mM to about 190 mM NaCl, or a salt gradient having an ionic strength equivalent thereto, and wherein the ionic strength is calculatable using a formula $I=\frac{1}{2}\Sigma_{i=1}^{n}c^{i}z_{i}^{2}$, where $c_i$ is the molar concentration of ion i (M, mol/L), $z_i$ is the charge number of that ion, and I is taken over all ions in the solution.

4. The method according to claim 1, wherein the genome-deficient AAV8 capsid intermediates are eluted from the anion exchange resin when a salt gradient reaches an ionic strength equivalent to about 50 mM NaCl or greater, or a salt gradient having an ionic strength equivalent thereto, and wherein the ionic strength is calculatable using a formula $I=\frac{1}{2}\Sigma_{i=1}^{n}c^{i}z_{i}^{2}$, where $c_i$ is the molar concentration of ion i (M, mol/L), $z_i$ is the charge number of that ion, and I is taken over all ions in the solution.

5. The method according to claim 1, wherein the method has a sample loading flow rate less than or equal to the elution flow rate.

6. The method according to claim 1, wherein the anion exchange resin is a quaternary amine strong anion exchange resin.

7. The method according to claim 1, wherein the anion exchange resin is in a column.

8. The method according to claim 1, wherein the affinity capture is performed using a high performance affinity resin.

9. A method for separating recombinant adeno-associated virus (AAV) 8 (rAAV8) viral particles from genome-deficient AAV8 capsid intermediates, said method comprising:
    (a) performing filtration through a series of depth filters to afford a clarified rAAV8 production culture harvest;
    (b) treating the clarified rAAV8 production culture harvest of (a) with a nuclease or a combination of nucleases to digest contaminating high molecular weight nucleic acid and to afford a mixture comprising rAAV8 viral particles and genome-deficient AAV8 capsid intermediates;
    (c) contacting the mixture of (b) comprising the rAAV8 viral particles and genome deficient AAV8 capsid intermediates with a high-performance AAV8-capsid binding affinity resin to afford a purified mixture;
    (d) mixing an affinity purified mixture of (c) comprising rAAV8 viral particles and genome-deficient AAV8 capsid intermediates and a first buffer at a neutral pH;
    (e) loading the suspension of (d) onto a strong anion exchange resin column;
    (f) washing the loaded strong anion exchange resin with a second buffer having a pH of about 10.2 and further comprising salt having an amount equivalent to 10 mM to 40 mM NaCl or a salt equivalent and Bis-Tris Propane (BTP);
    (g) applying an increasing salt concentration gradient to the loaded and washed strong anion exchange resin, wherein the salt gradient is sufficient to elute the rAAV8 viral particles; and
    (h) collecting rAAV8 viral particles which are at least about 90% purified from genome-deficient AAV8 capsid intermediates.

10. The method according to claim 9, wherein the rAAV8 viral particles and genome-deficient AAV8 capsid intermediates of step (c) have been affinity purified at a high salt concentration.

11. The method according to claim 9, wherein the strong anion exchange resin is a quaternary amine ion exchange resin.

12. The method according to claim 11, wherein the strong anion exchange resin column comprises trimethylamine and a support matrix comprising poly(glycidyl methacrylate-co-ethylene dimethacrylate).

13. The method according to claim 9, wherein the salt gradient of (g) is from about 10 mM to about 190 mM NaCl or a salt equivalent.

14. The method according to claim 9, wherein the strong anion exchange resin column is a monolith column and wherein column loading, washing, and elution occur in about 60 column volumes.

15. The method according to claim 9, wherein the elution in (g) has an elution flow rate which is from about 10 mL/min to about 40 mL/min.

16. The method according to claim 15, wherein the elution flow rate is about 20 mL/min.

17. The method according to claim 1, wherein the rAAV8 viral particles and the genome-deficient AAV8 capsid intermediates of step (d) have been affinity purified at a high salt concentration.

18. The method according to claim 1, wherein the series of depth filters of (a) comprise filters of 0.2 μm or greater pore size.

19. The method according to claim 1, wherein the series of depth filters of (a) comprise filters in the range of about 0.045 μm to about 0.2 μm pore size.

20. The method according to claim 1, wherein the anion exchange chromatography of (e) is performed at a pH of about 10.2.

21. The method according to claim 1, wherein genome-deficient AAV8 capsid intermediates are eluted from the anion exchange resin when a salt gradient reaches an ionic strength equivalent to about 50 mM KCl or greater, or a salt gradient having an ionic strength equivalent thereto, and wherein the ionic strength is calculatable using a formula $$I = \frac{1}{2}\sum_{i=1}^{n} c^i z_i^2,$$

where ci is the molar concentration of ion i (M, mol/L), $z_i$ is the charge number of that ion, and I is taken over all ions in the solution.

22. The method according to claim 9, wherein the series of depth filters of (a) comprise filters of 0.2 µm or greater pore size.

23. The method according to claim 9, wherein the series of depth filters of (a) comprise filters in the range of about 0.045 µm to about 0.2 µm pore size.

24. The method according to claim 9, wherein the washing buffer of (f) comprising BTP comprises 20 mM to 50 mM BTP.

* * * * *